(12) United States Patent
Kawase et al.

(10) Patent No.: US 7,578,914 B2
(45) Date of Patent: Aug. 25, 2009

(54) GAS CONCENTRATION MEASURING APPARATUS DESIGNED TO COMPENSATE FOR OUTPUT ERROR

(75) Inventors: Tomoo Kawase, Aichi-ken (JP); Eiichi Kurokawa, Okazaki (JP)

(73) Assignee: DENSO Corporation, Kariya (JP)

( * ) Notice: Subject to any disclaimer, the term of this patent is extended or adjusted under 35 U.S.C. 154(b) by 690 days.

(21) Appl. No.: 11/167,391

(22) Filed: Jun. 28, 2005

(65) Prior Publication Data
US 2005/0284759 A1   Dec. 29, 2005

(30) Foreign Application Priority Data
Jun. 28, 2004   (JP)   ............... 2004-190188

(51) Int. Cl.
*G01N 27/407*   (2006.01)
(52) U.S. Cl. .............. 204/426; 204/406; 204/410; 204/424; 205/784.5
(58) Field of Classification Search ............. None
See application file for complete search history.

(56) References Cited

U.S. PATENT DOCUMENTS 4,915,813 A * 4/1990 Nakajima et al. ........... 204/406

5,980,710 A   11/1999 Kurokawa et al.
6,226,861 B1   5/2001 Kurokawa et al.

FOREIGN PATENT DOCUMENTS

JP   11-37971   2/1999

* cited by examiner

*Primary Examiner*—Kaj K Olsen
*Assistant Examiner*—Kourtney R Salzman
(74) *Attorney, Agent, or Firm*—Nixon & Vanderhye P.C.

(57) ABSTRACT

A gas concentration measuring apparatus for use in air-fuel ratio control of motor vehicle engines is provided which is designed to determine the concentrations of oxygen at different resolutions within a wide and a narrow range using a first and a second sensor signal which are amplified by first and second operational amplifiers at different amplification factors. The apparatus samples values of the first sensor signal at different concentrations of oxygen to find an output characteristic error of the first operational amplifier and determines an actual concentration of oxygen to calculate an output characteristic error of the second operational amplifier using the one of the first operational amplifier and the actual concentration of oxygen. This permits values of the first and second sensor signals to be corrected so as to compensate for the output characteristics of the first and second operational amplifiers.

22 Claims, 11 Drawing Sheets

GAS CONCENTRATION MEASURING APPARATUS DESIGNED TO COMPENSATE FOR OUTPUT ERROR

CROSS REFERENCE TO RELATED DOCUMENT

The present application claims the benefit of Japanese Patent Application No. 2004-190188 filed on Jun. 28, 2004 the disclosures of which are incorporated herein by reference.

BACKGROUND OF THE INVENTION

Technical Field of the Invention relates generally to a gas concentration measuring apparatus which may be used in measuring the concentration of a preselected component, such as oxygen, of exhaust emissions of automotive engines, and more particularly to such a gas concentration measuring apparatus designed to correct an output of a gas sensor for compensating for an output error arising from individual variability of the apparatus.

BACKGROUND ART

Limiting current air-fuel (A/F) ratio sensors (also called A/F sensors or lambda sensors) are known which measure the concentration of oxygen ($O_2$) contained in exhaust emissions of motor vehicle engines to determine an air-fuel ratio of a mixture supplied to the engine. A typical one of the A/F sensors includes a sensor element made up of a solid electrolyte body and a pair of electrodes affixed to the solid electrolyte body. The measurement of concentration of oxygen is achieved by applying the voltage to the solid electrolyte body through the electrodes to produce a flow of electrical current through the sensor element as a function of the concentration of oxygen and sampling the electrical current to determine the A/F ratio.

In recent years, there has been a demand for measurement of the A/F ratio of the mixture to the engine in a wide range. For instance, it is required to measure the A/F ratio ranging from a rich to an extremely lean ratio equivalent in concentration of oxygen to the atmospheric air. In order to improve the accuracy of feedback control of the A/F ratio around the stoichiometry, it is also required to enhance the resolution at which the A/F ratio is measured around the stoichiometry. For example, Japanese Patent No. 3487159 (U.S. Pat. No. 5,980, 710) teaches an A/F ratio measuring system designed to amplify an output of an A/F sensor at two different amplification factors to determine the A/F ratio of a mixture to the engine at different resolutions within two ranges: a wide range of 11 to atmospheric air equivalent and a narrow range of 12 to 22.

Usually, the A/F sensors or sensor control circuits therefor have individual variability in circuit characteristics, which will result in a decrease in accuracy of measuring the A/F ratio. Further, A/F ratio measuring systems, like the one as taught in the above publication, designed to amplify a sensor output at different amplification factors to determine the A/F ratio in the wide and narrow ranges encounter the problem that measurement errors different between the wide and narrow ranges would arise from individual variability of resistors and/or operational amplifiers, thus increasing an error in correcting the A/F ratio, resulting in a decrease in accuracy of control of the A/F ratio of the mixture to the engine.

SUMMARY OF THE INVENTION

It is therefore a principal object of the invention to avoid the disadvantages of the prior art.

It is another object of the invention to provide a gas concentration measuring apparatus designed to find errors of gas concentration signals within different measurement ranges and compensate for such errors for improving the accuracy of measurement in the apparatus.

According to one aspect of the invention, there is provided a gas concentration measuring apparatus which may be employed in determining an air-fuel ratio of a mixture supplied to an automotive engine for use in combustion control of the engine. The gas concentration measuring apparatus is designed to sample an output of a gas concentration sensor which includes a sensor element made of a solid electrolyte body working to produce an electric current as a function of concentration of a given gas component and comprising: (a) a first signal output circuit designed to output a first sensor signal as a function of an electric current produced by the sensor element for use in determining a concentration of the given gas component in a first gas concentration range; (b) a second signal output circuit designed to output a second sensor signal as a function of the electric current for use in determining a concentration of the given gas component in a second gas concentration range different from the first gas concentration range; and (c) a gas concentration determining circuit working to sample the first and second sensor signals to determine the concentrations of the given gas component in the first and second gas concentration ranges. The gas concentration determining circuit analyzes a value of the first sensor signal to determine a first output characteristic error that is a difference between an actual output characteristic and a stated reference output characteristic of the first signal output circuit, samples values of the first sensor signal and the second sensor signals when the gas component lies within the second gas concentration range, calculates an actual concentration of the gas component using a concentration of the gas component indicated by the sampled value of the first sensor signal and the first output characteristic error, determines a difference between the value of he second sensor signal sampled upon calculation of the actual concentration of the gas component and a corresponding value of a stated reference output characteristic of the second signal output circuit as a second output characteristic error of the second signal output circuit.

In the preferred mode of the invention, the gas concentration determining circuit samples values of the first sensor signal at two different concentrations of the gas component and determines two output errors that are differences between the sampled values of the first sensor signal and corresponding values of the stated reference output characteristic of the first signal output circuit. The gas concentration determining circuit calculates the actual concentration of the gas component within the second gas concentration range using the determined two output errors.

The gas concentration determining circuit performs an interpolation operation on the two output errors of the first sensor signal to determine the actual concentration of the given gas component within the second gas concentration range.

The gas component may be oxygen. In this case, the first gas concentration range is between a 0% oxygen concentration and an air equivalent concentration that is a concentration of the oxygen equivalent to that of atmospheric air. The gas concentration determining circuit samples values of the first sensor signal at the 0% oxygen concentration and the air equivalent concentration to determine the two output errors.

The gas concentration measuring apparatus further comprises a sensor control circuit and a switching circuit. The sensor control circuit includes the first and second signal output circuits and works to apply a voltage to the sensor element to produce a flow of the electric current through the sensor element. The sensor control circuit operates in a first mode to sample the first and second sensor signals for use in determining the concentrations of the oxygen in the first and second gas concentration ranges and in a second mode to produce a reference sensor signal that is the value of the first sensor signal and indicates the 0% oxygen concentration. The switch works to switch between the first and second modes of the sensor control circuit when requested.

The gas concentration determining circuit samples a value of the second sensor signal at the 0% oxygen concentration and determines an output error that is a difference between the sampled value of the second sensor signal and a corresponding value of the stated reference output characteristic of the second signal output circuit and an output error that is a difference between the value of the second sensor signal sampled upon calculation of the actual concentration of the oxygen and a corresponding value of the stated reference output characteristic of the second signal output circuit. The apparatus further includes a correction circuit working to correcting a sampled value of the second signal output so as to compensate for the output errors of the second sensor signal.

The gas concentration determining circuit is designed to sample values of the first sensor signal at two concentrations of the gas component within the second gas concentration range to determine two actual concentrations of the gas component using the first output characteristic error. The gas concentration determining circuit determines two output errors that are differences between the sampled values of the first sensor signal and corresponding values of the stated reference output characteristic of the first signal output circuit and calculates the second output characteristic error using the two output errors. The correction circuit works to correct a sampled value of the second signal output so as to compensate for the second output characteristic error.

The first signal output circuit is designed to amplify an input thereto that is a function of the electrical current produced by the sensor element at a first amplification factor to output the first sensor signal. The second signal output is designed to amplify an input thereto that is a function of the electrical current produced by the sensor element at a second amplification factor different from the first amplification factor to output the second sensor signal.

The first amplification factor is smaller than the second amplification factor.

According to the second aspect of the invention, there is provided a gas concentration measuring apparatus designed to sample an output of a gas concentration sensor which includes a sensor element made of a solid electrolyte body working to produce an electric current as a function of concentration of oxygen of exhaust emissions of an internal combustion engine. The gas concentration measuring apparatus comprises: (a) a first signal output circuit designed to output a first sensor signal as a function of the electric current for use in determining a concentration of the oxygen in a wide concentration range including a stoichiometric oxygen concentration equivalent to a 0% oxygen concentration and an air equivalent concentration that is a concentration of oxygen equivalent to that of atmospheric air; (b) a second signal output circuit designed to output a second sensor signal as a function of the electric current for use in determining a concentration of the oxygen in a narrow concentration range including the stoichiometric oxygen concentration and excluding the air equivalent concentration; and (c) a gas concentration determining circuit working to sample the first and second sensor signals to determine the concentrations of the oxygen in the first and second gas concentration ranges. The gas concentration determining circuit samples values of the first sensor signal at the stoichiometric oxygen concentration and the air equivalent concentration, determines two output errors that are differences between the sampled values of the first sensor signal and corresponding values of a stated reference output characteristic of the first signal output circuit as a first output characteristic error of the first signal output circuit, samples values of the first sensor signal and the second sensor signals when the concentration of the oxygen lies within the second gas concentration range, calculates an actual concentration of the oxygen using a concentration of the oxygen indicated by the sampled value of the first sensor signal and the first output characteristic error of the first signal output circuit, and determines a difference between the value of the second sensor signal sampled upon calculation of the actual concentration of the oxygen and a corresponding value of a stated reference output characteristic of the second signal output circuit as a second output characteristic error of the second signal output circuit.

In the preferred mode of the invention, the gas concentration measuring apparatus further includes a sensor control circuit and a switching circuit. The sensor control circuit includes the first and second signal output circuits and works to apply a voltage to the sensor element to produce a flow of the electric current through the sensor element. The sensor control circuit operates in a first mode to sample the first and second sensor signals for use in determining the concentrations of the oxygen in the first and second gas concentration ranges and in a second mode to produce a reference sensor signal that is the value of the first sensor signal and indicates the 0% oxygen concentration. The switch works to switch between the first and second modes of the sensor control circuit when requested.

The gas concentration determining circuit samples a value of the second sensor signal at the 0% oxygen concentration and determines an output error that is a difference between the sampled value of the second sensor signal and a corresponding value of the stated reference output characteristic of the second signal output circuit and an output error that is a difference between the value of the second sensor signal sampled upon calculation of the actual concentration of the oxygen and a corresponding value of the stated reference output characteristic of the second signal output circuit. The apparatus further includes a correction circuit working to correcting a sampled value of the second signal output so as to compensate for the output errors of the second sensor signal.

The gas concentration determining circuit is designed to sample values of the first sensor signal at two concentrations of the oxygen within the second gas concentration range to determine two actual concentrations of the oxygen using the first output characteristic error. The gas concentration determining circuit determines two output errors that are differences between the sampled values of the first sensor signal and corresponding values of the stated reference output characteristic of the first signal output circuit and calculates the second output characteristic error using the two output errors. The correction circuit works to correct a sampled value of the second signal output so as to compensate for the second output characteristic error.

The first signal output circuit is designed to amplify an input thereto that is a function of the electrical current produced by the sensor element at a first amplification factor to output the first sensor signal. The second signal output is designed to amplify an input thereto that is a function of the electrical current produced by the sensor element at a second amplification factor different from the first amplification factor to output the second sensor signal.

The first amplification factor is smaller than the second amplification factor.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
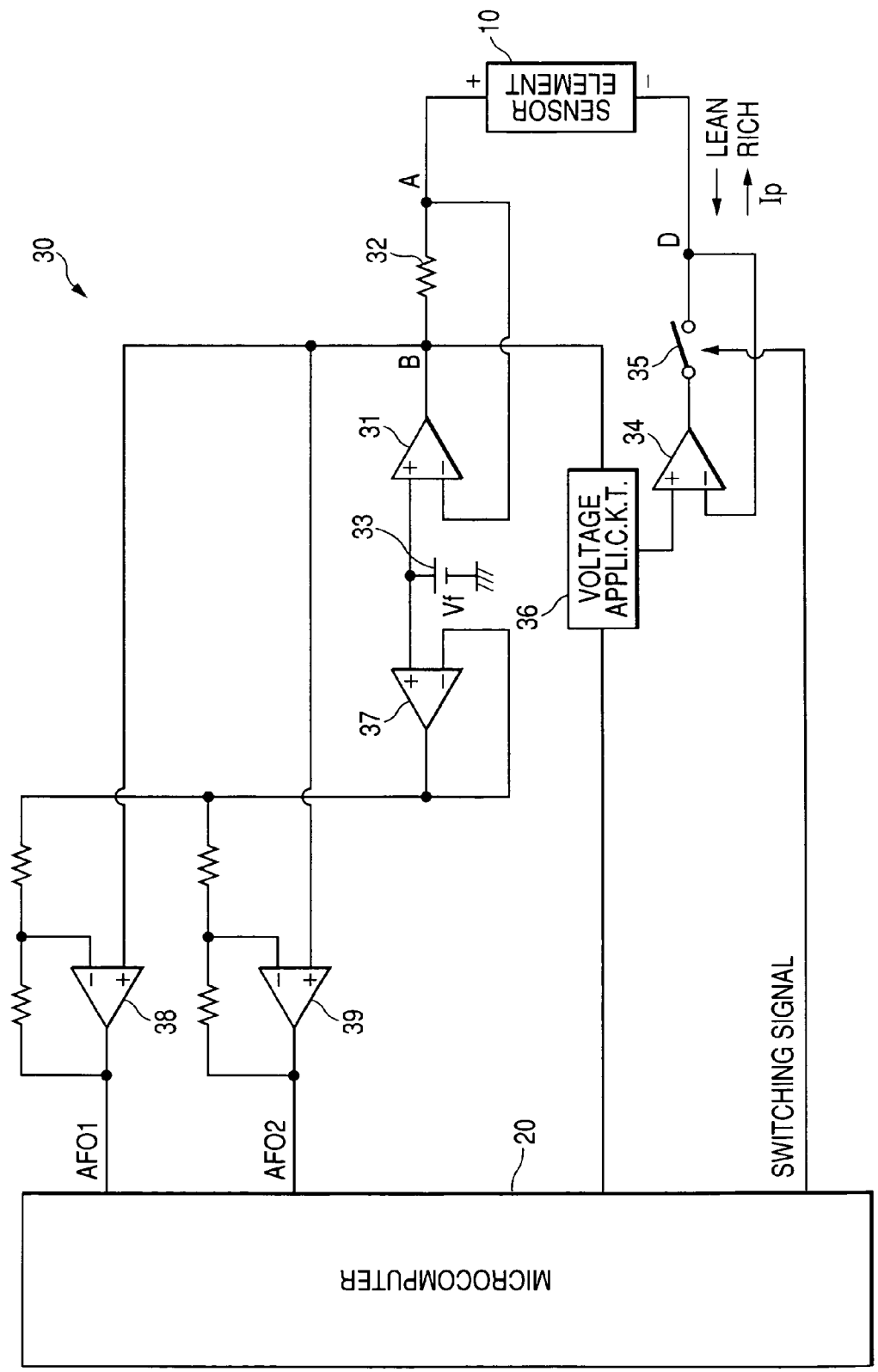
FIG. 1 is a circuit diagram which shows an electric structure of a gas concentration measuring apparatus according to the first embodiment of the invention.

Referring to the drawings, wherein like reference numbers refer to like parts in several views, particularly to FIG. 1, there is shown a gas concentration measuring apparatus designed to measure the concentration of oxygen ($O_2$) contained in exhaust emissions of an automotive engine which corresponds to an air-fuel ratio (AFR) of a mixture supplied to the engine. The measured concentration is used in an air-fuel ratio control system implemented by an engine electronic control unit (ECU). The air-fuel ratio control system works to perform a stoichiometric burning control to regulate the air-fuel ratio of the mixture around the stoichiometric air-fuel ratio under feedback control and a lean-burn control to bring the air-fuel ratio to within a given lean range under feedback control.

The gas concentration measuring apparatus includes a microcomputer 20, a sensor control circuit 30, and an oxygen sensor (will be referred to as an air-fuel (A/F) sensor below) which works to produce a current signal as a function of concentration of oxygen contained in exhaust emissions introduced into a gas chamber formed in the A/F sensor.

Figure 2:
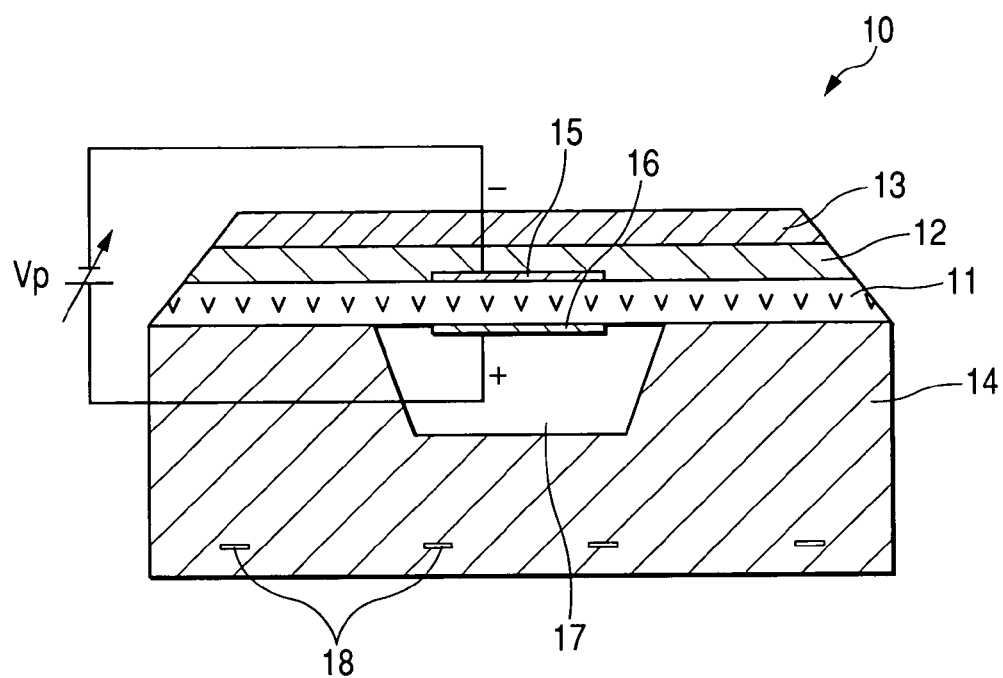
FIG. 2 is a transverse sectional view which shows a sensor element used in the gas concentration measuring apparatus as illustrated in FIG. 1.

The A/F sensor includes a laminated sensor element 10 which has a sectional structure, as illustrated in FIG. 2. The sensor element 10 has a length extending perpendicular to the drawing surface of FIG. 2 and is, in practice, disposed within a sensor housing and a protective cover. The A/F sensor is installed in an exhaust pipe of the engine. For instance, EPO 987 546 A2, assigned to the same assignee as that of this application teaches a structure and control of an operation of this type of gas sensor in detail, disclosure of which is incorporated herein by reference.

The sensor element 10 is made up of a solid electrolyte layer 11, a diffusion resistance layer 12, a shielding layer 13, and an insulating layer 14 which are laminated or stacked vertically as viewed in the drawing. The sensor element 10 is surrounded by a protective layer (not shown). The solid electrolyte layer 11 is made of a rectangular partially-stabilized zirconia sheet and has upper and lower electrodes 15 and 16 affixed to opposed surfaces thereof. The electrodes 15 and 16 are made of platinum (Pt), for example. The diffusion resistance layer 12 is made of a porous sheet which permits exhaust gasses to flow to the electrode 15. The shielding layer 13 is made of a dense sheet which inhibits the exhaust gasses from passing therethrough. The layers 12 and 13 are each formed using a sheet made of ceramic such as alumina or zirconia and have average porosities, or gas permeability different from each other.

The insulating layer 14 is made of ceramic such as alumina or zirconia and has formed therein an air duct 17 to which the electrode 16 is exposed. The insulating layer 14 has a heater 18 embedded therein. The heater 18 is made of heating wire which is supplied with power from a storage battery installed in the vehicle to produce heat the whole of the sensor element 10 up to a desired activation temperature. In the following discussion, the electrode 15 will also be referred to as a diffusion resistance layer side electrode, and the electrode 16 will also be referred to as an atmosphere side electrode. The atmosphere side electrode 16 is connected to a positive (+) terminal of a power source, while the diffusion resistance layer side electrode 15 is connected to a negative (−) terminal of the power source.

The exhaust gasses flowing within an exhaust pipe of the engine to which the sensor element 10 is exposed enter and pass through the side of the diffusion resistance layer 12 and reach the diffusion resistance layer side electrode 15. When the exhaust gasses are in a fuel lean state (more oxygen), oxygen molecules contained in the exhaust gasses are decomposed or ionized by application of voltage between the electrodes 15 and 16, so that they are discharged to the air duct 17 through the solid electrolyte layer 11 and the electrode 16. This will cause a positive current to flow from the atmosphere side electrode 16 to the diffusion resistance layer side electrode 15. Alternatively, when the exhaust gasses are in a fuel rich state (less oxygen), oxygen molecules contained in air within the air duct 17 are ionized by the electrode 16 so that they are discharged into the exhaust pipe through the solid electrolyte layer 11 and the electrode 15 and undergo catalytic reaction with unburned components such as HC or CO in the exhaust gasses. This will cause a negative current to flow from the diffusion resistance layer side electrode 15 to the atmosphere side electrode 16. The operation of the A/F sensor is well known in the art, and explanation thereof in detail will be omitted here.

Figure 3:
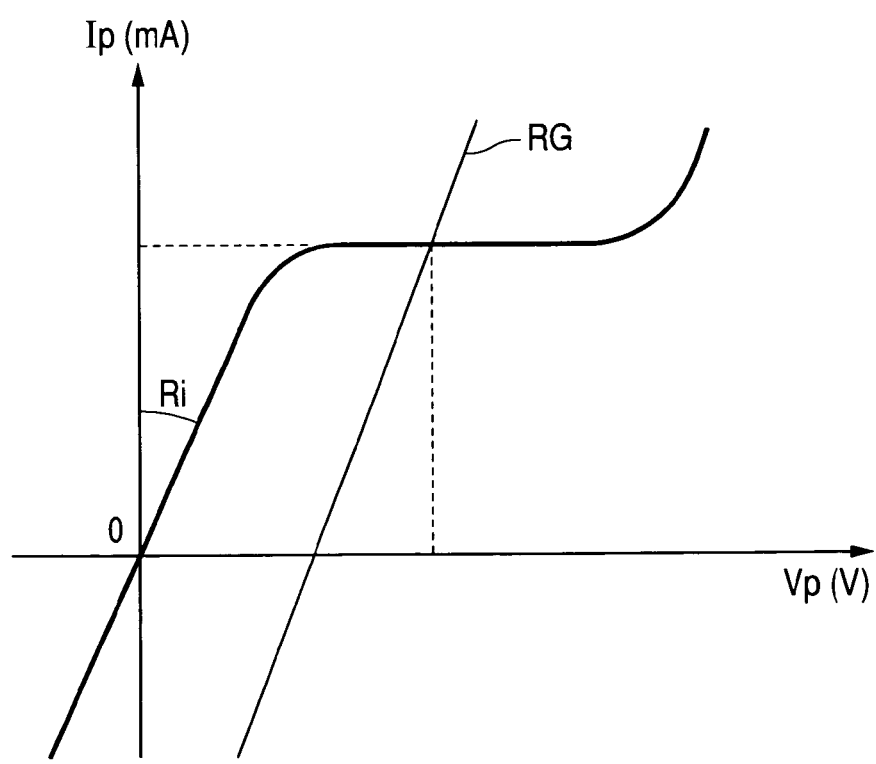
FIG. 3 shows an example of an applied voltage-to-output current map for use in determining a target voltage to be applied to the sensor element as illustrated in FIG. 2.

FIG. 3 shows a typical voltage-to-current relation (i.e., V-I characteristic) of the A/F sensor. A straight segment of a V-I curve extending parallel to the abscissa axis (i.e., V-axis) indicate a limiting current range within which the sensor element 10 produces an electric current Ip (i.e., a limiting current) as a function of an air-fuel ratio (i.e., richness or leanness). Specifically, as the air-fuel ratio changes to the lean side, the current Ip produced by the sensor element 10 increases, while as the air-fuel ratio changes to the rich side, the current Ip decreases. The current Ip will also be referred to as a sensor element current below.

A portion of the V-I curve lower in voltage than the limiting current range represents a resistance-dependent range. An inclination of a first-order segment of the V-I curve depends upon dc internal resistance Ri of the sensor element 10. The dc internal resistance Ri changes with a change in temperature of the sensor element 10. Specifically, it increases with a decrease in temperature of the sensor element 10, so that the inclination of the first-order segment of the V-I curve in the resistance-dependent range is decreased. Alternatively, when the temperature of the sensor element 10 rises, it results in a decrease in the dc internal resistance Ri, so that the inclination of the first-order segment of V-I curve is increased. A line RG indicates a target voltage Vp to be applied to the sensor element 10 (i.e., the electrodes 15 and 16).

Referring back to FIG. 1, the gas concentration measuring apparatus, as described above, includes the sensor control circuit 30 and the microcomputer 20 and works to control an operation of the A/F sensor to determine an air-fuel ratio of a mixture supplied to the engine and also calculate the impedance Zac of the sensor element 10 (which will also be referred to as a sensor element impedance below).

The microcomputer 20 is made of a known arithmetic logic unit consisting of a CPU, memories, A/D converters, and I/O ports and works to sample an analog sensor signal, as produced by the sensor control circuit 30, through the A/D converter to determine the A/F ratio and the sensor element impedance Zac. The A/F ratio, as determined by the microcomputer 20, is outputted to the engine ECU (not shown) for use in the air-fuel ratio feedback control.

The sensor control circuit 30 connects with the sensor element 10 through a positive (+) terminal and a negative (−) terminal. The positive terminal leads to the atmosphere side electrode 16 of the sensor element 10, while the negative terminal leads to the diffusion resistance layer side electrode 15. The sensor control circuit 30 also includes operational amplifiers 31 and 34, a current-measuring resistor 32, a reference voltage source 33, a switch 35, and a voltage application control circuit 36. The positive terminal of the sensor element 10 also connects with the reference voltage circuit 33 through the current-measuring resistor 32 and the operational amplifier 31. The negative terminal also connects with the voltage application control circuit 36 through the operational amplifier 34 and the switch 35. The voltage appearing at a junction A of an end of the current-measuring resistor 32 and the positive terminal of the sensor element 10 is kept at the same level as that of the reference voltage source 33 (i.e., a reference voltage Vf of 2.2 V, for example). The sensor element current Ip flows through the current-measuring resistor 32. The voltage appearing at a junction B changes with a change in the sensor element current Ip. When the exhaust gas of the engine is in a fuel lean state, that is, the exhaust gas results from burning of a lean mixture, and the switch 35 is in an on-state or closed, the sensor element current Ip flows from the positive terminal to the negative terminal through the sensor element 10, so that the voltage at the junction B rises. Conversely, when the exhaust gas is a fuel rich state, the sensor element current Ip flows from the negative terminal to the positive terminal through the sensor element 10, so that the voltage at the junction B drops.

The voltage application control circuit 36 works to monitor the voltage at the junction B and determine the target voltage Vp to be applied to the sensor element 10 as a function of the monitored voltage, for example, by look-up using the target applying voltage line RG, as illustrated in FIG. 3. The voltage application control circuit 36 then controls the operational amplifier 34 and the switch 35 to bring the voltage at the junction D into agreement with the target voltage Vp. If it is required only to measure the A/F ratio (i.e., the sensor element current Ip) near the stoichiometric one, the voltage application control circuit 36 may keep the voltage to be applied to the sensor element 10 at a constant level.

The sensor control circuit 30 also includes operational amplifiers 37, 38, and 39. The reference voltage source 33 connects with the operational amplifier 37. The operational amplifiers 38 and 39 each work as a differential amplifier having a given amplification factor to which an output of the operational amplifier 37 and the voltage at the junction B are inputted. Specifically, the operational amplifiers 38 and 39 amplify a difference between the reference voltage Vf and the voltage at the junction B and outputs it as A/F output voltages AFO1 and AFO2 to the microcomputer 20, respectively. The operational amplifier 38 has an amplification factor of five (5), while the operational amplifier 39 has an amplification factor of fifteen (15).

The microcomputer 20 analyzes the A/F output voltage AFO1 inputted from the operational amplifier 38 and determines the A/F ratio of the mixture within a full AFR measurement range (e.g., A/F=11 to air-to-fuel free ratio (i.e., an extremely lean A/F ratio)). The microcomputer 20 also analyzes the A/F output voltage AFO2 inputted from the operational amplifier 39 and determines the A/F ratio of the mixture within a narrow AFR measurement range (e.g., A/F=12 to 22) including the stoichiometric A/F ratio. In the following discussion, the output voltages AFO1 and AFO2 will also be referred to as an AFR wide range measuring signal and a stoichiometric air-fuel ratio (AFR) measuring signal, respectively.

Each of the operational amplifiers 38 and 39 may alternatively be designed to receive the voltages developed at the junctions A and B in order to amplify the difference between the reference voltage Vf and the voltage at the junction B. This arrangement, however, encounters the drawback in that the feedback currents of the operational amplifiers 38 and 39 flow through the current-measuring resistor 32, which may lead to an error in determining the A/F ratio. In order to avoid this, each of the operational amplifiers 38 and 39 is designed to receive the output of the operational amplifier 37 and the voltage at the junction B to have the operational amplifier 37 function as a feedback current absorber in order to maintain the reliability in determining the A/F ratio.

The microcomputer 20 works to sample the A/F output voltages AFO1 and AFO2 through the A/D ports and determine an instantaneous value of the A/F ratio of a mixture supplied to the engine for use in the air-fuel ratio feedback control.

The microcomputer 20 also works to sweep the voltage applied to the sensor element 10 instantaneously in an ac form to determine the sensor element impedance Zac (i.e., an internal resistance of the sensor element 10) using a resulting change in the current Ip flowing through the sensor element 10. Specifically, when an impedance measuring mode, as will be described later, is entered, the microcomputer 20 outputs an impedance measuring command signal to the voltage application control circuit 36. The voltage application control circuit 36 then applies the voltage to the sensor element 10 and change it (i.e., the voltage at the junction D) in sequence by a given level (e.g., 0.2V) to the positive and negative sides. This causes the sensor element current Ip flowing through the sensor element 10 to change, thus resulting in a change in voltage developed at the junction B. The microcomputer 20 monitors the change in voltage at the junction B, calculates a current change $\Delta I$ by dividing the monitored change by a resistance value of the current-measuring resistor 32, and divides a change in voltage $\Delta V$ applied to the sensor element 10 by the current change $\Delta I$ to determine the sensor element impedance Zac ($=\Delta V/\Delta I$). The determination of the sensor element impedance Zac may alternatively be made by supplying the current to the sensor element 10, sweeping it in an ac form, and monitoring a resultant change in current or voltage provided by the sensor element 10. U.S. Pat. No. 6,578,563 B2, issued Jun. 17, 2003, assigned to the same assignee as that of this application teaches how to determine the sensor element impedance Zac, disclosure of which is incorporated herein by reference.

The determination of the sensor element impedance Zac is performed at a preselected regular time interval. Specifically, the microcomputer 20, as described above, outputs the impedance measuring command signal to the voltage application control circuit 36 in a given cycle. The microcomputer 20 also works to control an electric power supplied to the heater 18 so as to keep the sensor element impedance Zac at a given target value so that the sensor element 10 is held at a selected temperature to maintain a desired activation status where the sensor element 10 produces an output as a function of the A/F ratio correctly.

Figure 4A:
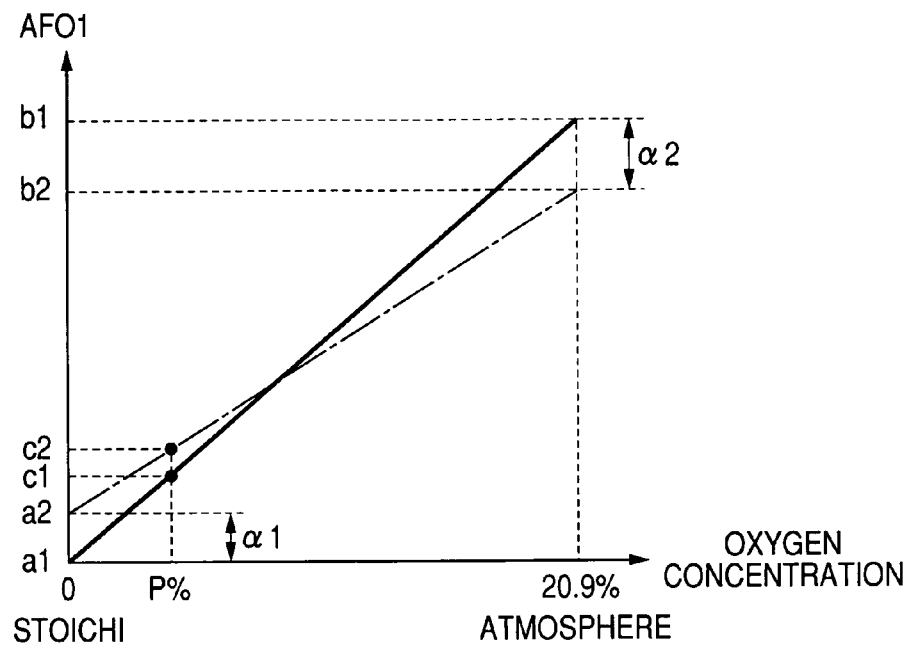
FIG. 4(a) is a graph which demonstrates an offset error and a gain error of an output of an operational amplifier used in determining an air-fuel ratio within a wide measurement range.
Figure 4B:
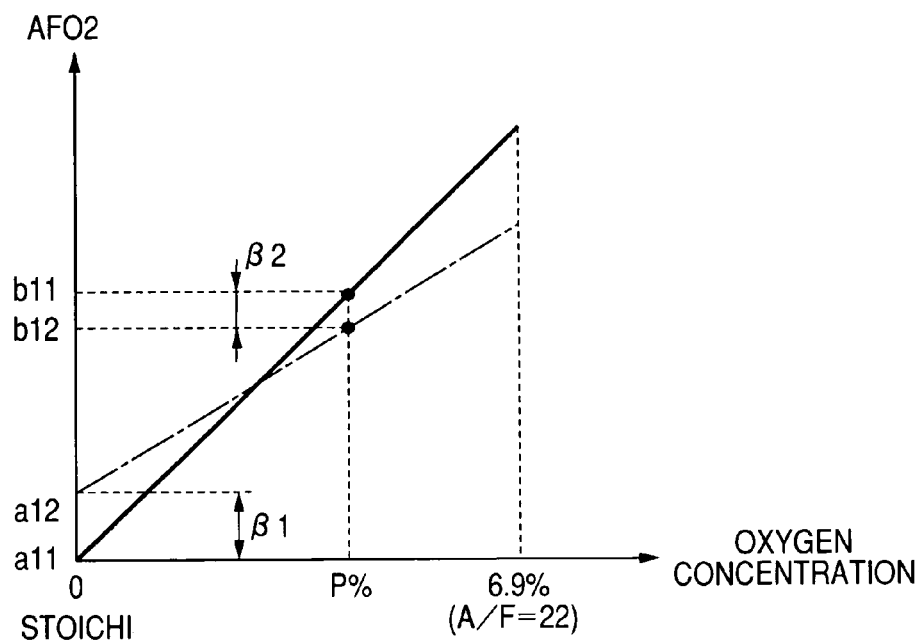
FIG. 4(b) is a graph which demonstrates an offset error and a gain error of an output of an operational amplifier used in determining an air-fuel ratio within a narrow measurement range.

Usually, the A/F sensor and the sensor control circuit 30 each have individual variability or unit-to-unit variation in characteristics thereof which may result in decreased accuracy of output of the A/F sensor. FIG. 4(a) demonstrates output characteristics of the operational amplifier 38 which represent a change in the AFR wide range measuring signal AFO1 (i.e., the output of the operational amplifier 38) with a change in the concentration of oxygen within the full AFR measurement range from the stoichiometric A/F ratio to an air-to-fuel free ratio (i.e., 0% to 20.9% in terms of the concentration of oxygen). FIG. 4(b) demonstrates output characteristics of the operational amplifier 39 which represent a change in the stoichiometric AFR measuring signal AFO2 (i.e., the output of the operational amplifier 39) with a change in the concentration of oxygen within the narrow AFR measurement range from the stoichiometric A/F ratio to an A/F ratio of 22 (i.e., 0% to 6.9% in terms of the concentration of oxygen). In FIG. 4(a), a solid line indicates a reference output characteristic defined by a set of reference values of the AFR wide range measuring signal AFO1 which are to be produced by the operational amplifier 38 as indicating a correct concentration of oxygen in the exhaust gas. A broken line indicates an actual output characteristic defined by a set of actually attained values of the AFR wide range measuring signal AFO1. It has been noted that a difference between the reference value and actually attained value of the AFR wide range measuring signal AFO1 arises from two types of errors: an offset error and a gain error. The offset error is a shift of the AFR wide range measuring signal AFO1 from zero (0) which occurs when the exhaust gas of the engine is in an atmosphere where the A/F ratio of a mixture supplied to the engine is stoichiometric. The gain error is a shift of an inclination of the broken line from the solid line, that is, a difference in change rate between the actually attained value and the reference value of the AFR wide range measuring signal AFO1. The same applies to the stoichiometric AFR measuring signal AFO2 in FIG. 4(b).

The AFR wide range measuring signal AFO1 and the stoichiometric AFR measuring signal AFO2 are produced by the operational amplifiers 38 and 39 which are independent in operation and thus thought of as having output errors different in magnitude from each other. The elimination of such errors requires analysis of individual output characteristics of the operational amplifiers 38 and 39. The error of each of the signals AFO1 and AFO2 at any concentration of oxygen in the exhaust gas of the engine may be found by measuring differences between the actually attained value and the reference value of each of the signals AFO1 and AFO2 at at least two different concentrations of oxygen and calculating the actual output characteristic of a corresponding one of the amplifiers 38 and 39 through the interpolation operation on the measured differences. In the case of the output characteristics of the operational amplifier 38 in FIG. 4(a), an error of the signal AFO1 at any concentration of oxygen may be found by measuring errors thereof when the exhaust gas is stoichiometric and when the exhaust gas is identical in concentration of oxygen with the atmospheric air. These two conditions may be created by turning off or opening the switch 35 of the sensor control circuit 30 and cutting the supply of fuel to the engine. Specifically, the sensor control circuit 30 may be placed in a mode of operation equivalent to when the sensor element 10 is measuring the stoichiometric exhaust gas of the engine by turning off the switch 35 and in a mode of operation equivalent to when the sensor element 10 is measuring the exhaust gas equivalent in concentration of oxygen to the atmospheric air by cutting the supply of fuel to the engine. The two modes of operation of the sensor control circuit 30 will also be referred to as a virtual stoichiometric AFR measuring mode and an atmospheric air emission measuring mode below.

In the case of the output characteristics of the operational amplifier 39 in FIG. 4(b), it is possible to measure an error of the signal AFO2 when the sensor control circuit 30 is placed in the virtual stoichiometric AFR measuring mode, but however, another error required by the interpolation is difficult to measure. This is because the measurement range of the stoichiometric AFR measuring signal AFO2 is 12 to 22 in terms of the A/F ratio, and it is impossible to place the sensor control circuit 30 in a condition equivalent to when the sensor element 10 measures a known concentration of oxygen in the exhaust gas, that is, when the sensor element 10 measures the concentration of oxygen equivalent to that in the atmospheric air.

In order to eliminate the above problem, the microcomputer 20 is, as will be described later in detail, designed to sample and analyze the AFR wide range measuring signal AFO1 when the exhaust gas lies within the narrow A/F measuring range to find an output characteristic error of the operational amplifier 38 that is a difference between the actual output characteristic and the reference output characteristic of the operational amplifier 38, search the reference value of the signal AFO1 when the exhaust gas has any concentration of oxygen to calculate a correct concentration of the oxygen, sample the stoichiometric AFR measuring signal AFO2 upon the calculation of the correct concentration of the oxygen, and determine the output characteristic error (i.e., the sum of the offset and gain errors) of the operational amplifier 39 based on the sampled value of the signal AFO2 and a corresponding one of the reference values of the signal AFO2.

Specifically, if the operational amplifier 38 has the reference output characteristic, as represented by the solid line in FIG. 4(a), the AFR wide range measuring signal AFO1 has a value a1 (e.g., 2.2V) when the sensor control circuit 30 is placed in the virtual stoichiometric AFR measuring mode and a value b1 (e.g., 4.1V) when the sensor control circuit 30 is placed in the atmospheric air emission measuring mode. Alternatively, if the operational amplifier 38 has the actual output characteristic, as represented by the broken line in FIG. 4(a), the AFR wide range measuring signal AFO1 has a value a2 when the sensor control circuit 30 is placed in the virtual stoichiometric AFR measuring mode and a value b2 when the sensor control circuit 30 is placed in the atmospheric air emission measuring mode. Therefore, errors of the signal AFO1 in the virtual stoichiometric AFR measuring mode and the atmospheric air emission measuring mode will be $\alpha 1$ and $\alpha 2$, respectively. When the concentration of oxygen in the exhaust gas is P %, the reference output characteristic provides the signal AFO1=c1, while the actual output characteristic provides the signal AFO1=c2.

Figure 5:
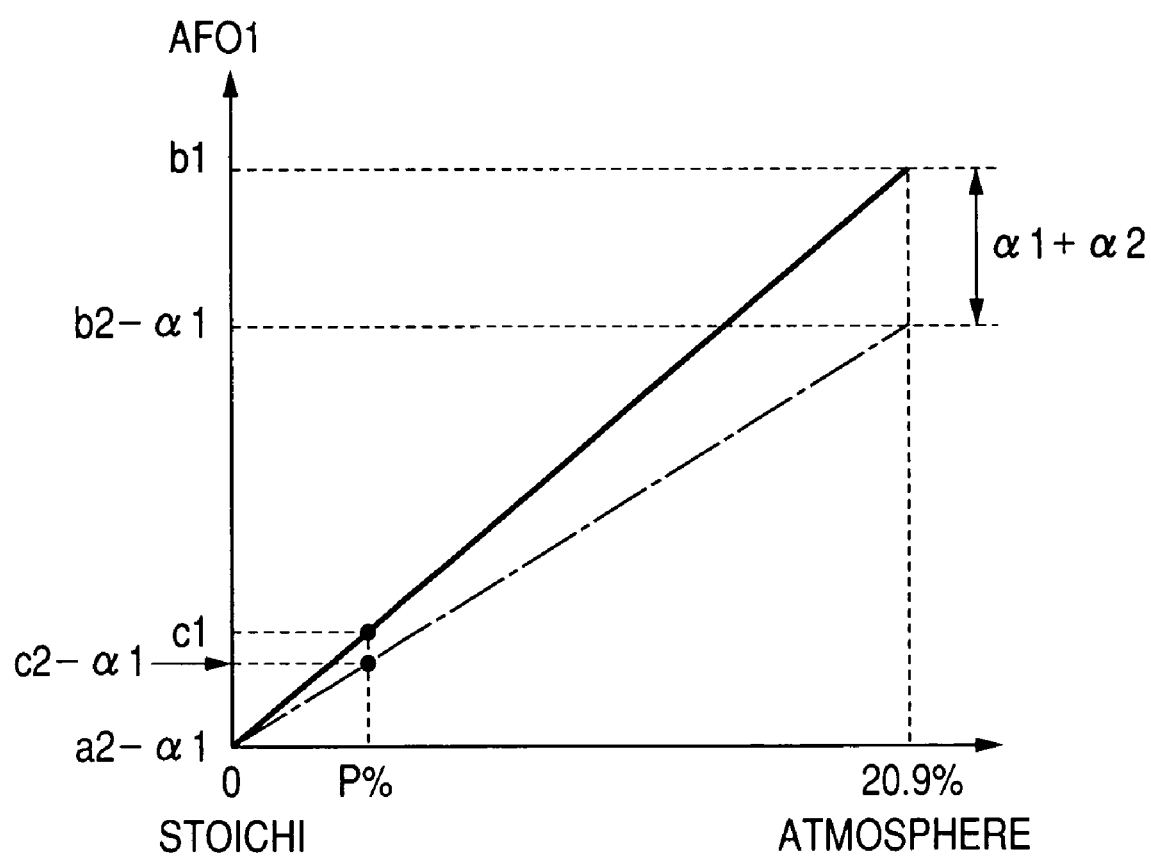
FIG. 5 is a graph which represents a relation between an actual output characteristic and a reference output characteristic of an operation amplifier used in determining an air-fuel ratio within a wide measurement range.

For the sake of understanding, FIG. 5 shows the relation between the actual output characteristic, as represented by the broken line, and the reference output characteristic, as represented by the solid line, in which the actual output characteristic is shifted to the negative (−) side by the output error $\alpha 1$ to agree with the reference output characteristic at a time when the sensor control circuit 30 is placed in the virtual atmospheric AFR measuring mode. From the illustrated relation, any value of the signal AFO1 on the reference output characteristic (i.e., AFO1=c1) is found to be given by $$c1 = c2 + \frac{c2-a2}{b2-a2} \times (a1+a2) - \alpha 1 \qquad (1)$$

Therefore, when the exhaust gas has any concentration of oxygen (i.e., P %), a correct concentration of the oxygen may be calculated using Eq. (1). This enables the gain error $\beta 2$ of the stoichiometric AFR measuring signal AFO2 when the concentration of oxygen in the exhaust gas is P % to be determined. The offset error $\beta 1$ of the signal AFO2 is calculated as a difference between an actual value of the signal AFO2 (i.e., a12) and a value thereof on the reference output characteristic (i.e., a11) when the sensor control circuit 30 is placed in the virtual stoichiometric AFR measuring mode. The offset and gain errors $\beta 1$ and $\beta 2$ of the stoichiometric AFR measuring signal AFO2 thus determined may be used to determine the output characteristic error of the operational amplifier 39 for use in compensating for the offset and gain errors $\beta 1$ and $\beta 2$ of the stoichiometric AFR measuring signal AFO2.

The offset errors $\alpha 1$ and $\beta 1$ of the signals AFO1 and AFO2 are, as described above, found by opening the switch 35 of the sensor control circuit 30 temporarily during running of the engine to place the sensor control circuit 30 in the virtual stoichiometric AFR measuring mode and sampling instantaneous values of the signals AFO1 and AFO2.

Figure 6:
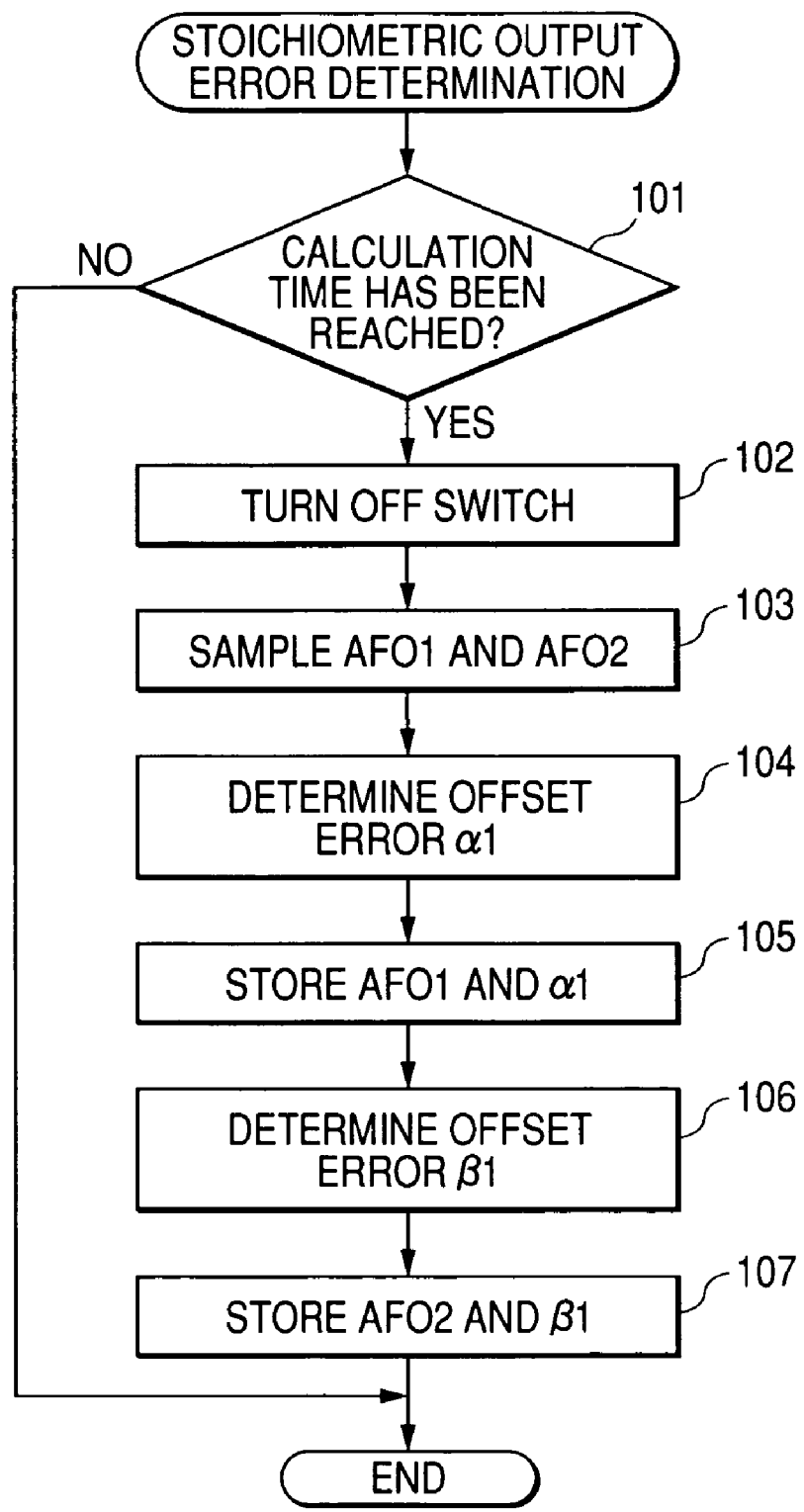
FIG. 6 is a flowchart of a program to be executed in the gas concentration measuring apparatus of FIG. 1 to determine offset errors of outputs of operational amplifiers used in determining an air-fuel ratio within wide and narrow measurement ranges.

FIG. 6 is a flowchart of a sequence of logical steps or program to be performed by the microcomputer 20 to determine stoichiometric output errors (i.e., the offset errors) of the AFR wide range measuring signal AFO1 and the stoichiometric AFR measuring signal AFO2 produced by the operational amplifiers 38 and 39.

After entering the program, the routine proceeds to step 101 wherein it is determined whether the time has been reached to calculate stoichiometric output errors (i.e., the offset errors $\alpha 1$ and $\beta 1$) or not, that is, whether the sensor control circuit 30 should be brought into the virtual stoichiometric AFR measuring mode to determine the offset errors $\alpha 1$ and $\beta 1$ of the signals AFO1 and AFO2 or not. For instance, the time is determined to have been entered every lapse of a period of time of, for example, 10 minutes, a few ten minutes, or a few hours. The time may alternatively be determined to have been entered when the A/F output voltages AFO1 and AFO2 are not used in the air-fuel ratio feedback control, for example, before the A/F sensor becomes activate, during a fuel cut-off mode of the engine, or when a main relay is controlled to keep the microcomputer 20 turned on for a given short period of time after an ignition switch of the vehicle is turned off.

If a NO answer is obtained, then the routine terminates. Alternatively, if a YES answer is obtained, then the routine proceeds to step 102 wherein an off-switching signal is outputted to the switch 35 to open it for a preselected period of time (e.g., 5 msec.).

The routine proceeds to step 103 wherein instantaneous values of the A/F output voltages AFO1 and AFO2 are sampled. The routine proceeds to step 104 wherein the offset error $\alpha 1$ (i.e., the stoichiometric output error) of the A/F output voltage AFO1 is determined. Specifically, a difference between the value of the A/F output voltage AFO1, as sampled in step 103, and a stoichiometric reference value is calculated as the offset error $\alpha 1$. The stoichiometric reference value is a value of the A/F output voltage AFO1 which is to be attained correctly when the exhaust gas is at the stoichiometric A/F ratio and set to 2.2V in this embodiment.

The routine proceeds to step 105 wherein the value of the A/F output voltage AFO1, as sampled in step 103, and the offset error a1, as calculated in step 104, are stored in a memory installed in the microcomputer 20.

The routine proceeds to step 106 wherein the offset error $\beta 1$ (i.e., the stoichiometric output error) of the A/F output voltage AFO2 is determined. Specifically, a difference between the value of the A/F output voltage AFO2, as sampled in step 103, and the stoichiometric reference value (i.e., 2.2V) is calculated as the offset error $\beta 1$. The routine proceeds to step 107 wherein the value of the A/F output voltage AFO2, as sampled in step 103, and the offset error $\beta 1$, as calculated in step 106, are stored in a memory installed in the microcomputer 20.

Figure 7:
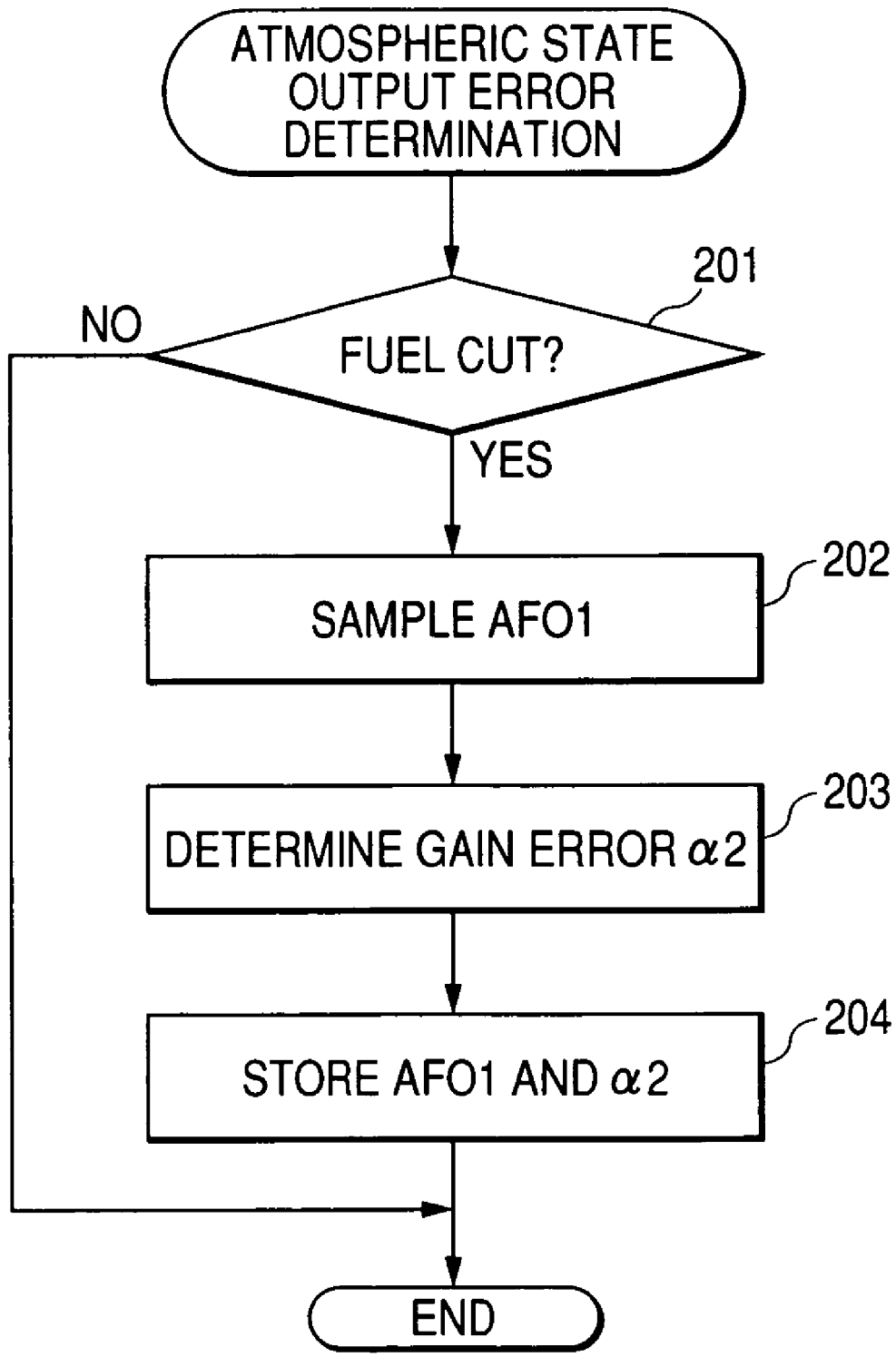
FIG. 7 is a flowchart of a program to determine a gain error of an output of an operational amplifier used in determining an air-fuel ratio in a wide measurement range.

FIG. 7 is a flowchart of a program to be executed by the microcomputer 20 to determine an atmospheric state output error (i.e., the gain error $\alpha 2$) of the A/F output voltage AFO1 produced by the operational amplifier 38. The gain error $\alpha 2$ usually arises from an error in adjustment of gains of the operational amplifiers 31, 34, 37, and/or 38.

First, in step 201, it is determined whether the engine is now undergoing a fuel cut or not. This determination is made to determine whether a condition which permits the gain error $\alpha 2$, as produced when the exhaust gas is in the atmospheric state, to be sampled is met or not. If a YES answer is obtained meaning that the gain error $\alpha 2$ sampling permissible condition is met, then the routine proceeds to step 202 wherein an instantaneous value of the A/F output voltage AFO1 is sampled. The routine proceeds to step 203 wherein the gain error α2 is determined by subtracting an atmospheric state reference value from the value of the A/F output voltage AFO1, as sampled in step 202. The atmospheric state reference value is a value of the A/F output voltage AFO1 which is to be attained correctly when the exhaust gas is in the atmospheric state and set to 4.1 V in this embodiment.

The routine proceeds to step 204 wherein the value of the A/F output voltage AFO1, as sampled in step 202, and the gain error α2, as calculated in step 204, are stored in a memory installed in the microcomputer 20. The routine then terminates.

Figure 8:
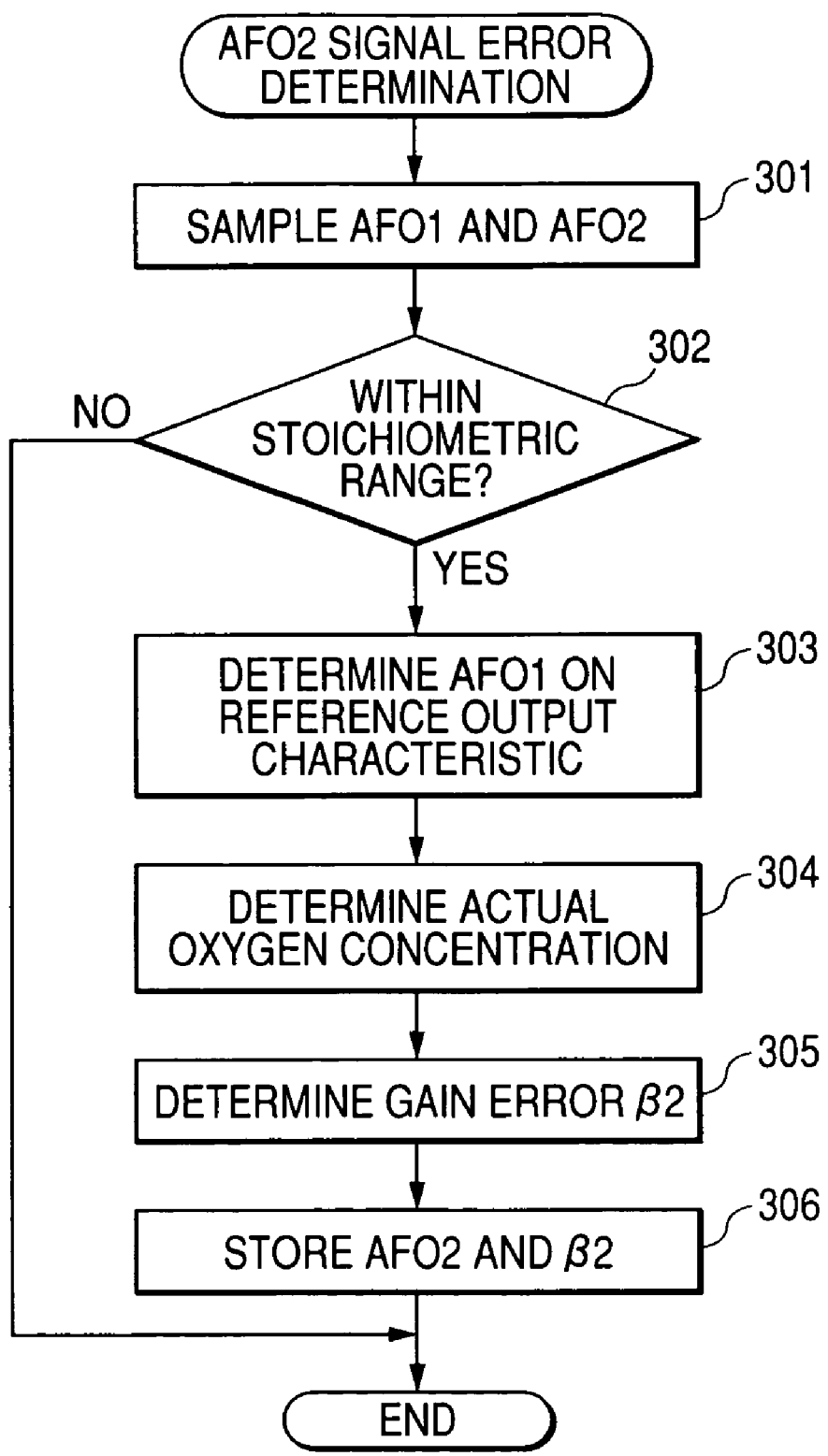
FIG. 8 is a flowchart of a program to determine an error of an output of an operational amplifier used in determining an air-fuel ratio in a narrow measurement range when an exhaust gas of the engine has any concentration of oxygen.

FIG. 8 is a flowchart of a program to be executed by the microcomputer 20 to determine the gain error β2 of the stoichiometric AFR measuring signal AFO2.

First, in step 301, values of the signals AFO1 and AFO2 are sampled.

The routine proceeds to step 302 wherein it is determined whether the current concentration of oxygen in the exhaust gas, as derived using the sampled value of the signal AFO1, lies within a stoichiometric range of 12 to 22 in terms of the A/F ratio (i.e., the narrow AFR measuring range) or not. If a NO answer is obtained, then the routine terminates. Alternatively, if a YES answer is obtained, then the routine proceeds to step 303 wherein the value of the signal AFO1 on the reference output characteristic of the operational amplifier 38 corresponding to the concentration of oxygen, as derived in step 302, is estimated using Eq. (1), as described above. Specifically, the value (i.e., c2 in FIG. 4(a)) of the signal AFO1, as sampled in step 301, the value (i.e., a2 in FIG. 4(a)) of the signal AFO1, as sampled in the stoichiometric AFR measuring mode and stored in step 105 of FIG. 6, the offset error α1, as derived and stored in step 105 of FIG. 6, the value (i.e., b2 in FIG. 4(a)) of the signal AFO1, as derived in the atmospheric air emission measuring mode and stored in step 204 of FIG. 7, and the gain error α2, as derived and stored in step 204 of FIG. 7, are used to determine the value (i.e., c1 in FIG. 4(a)) of the signal AFO1 on the reference output characteristic according to Eq. (1).

After step 303, the routine proceeds to step 304 wherein a correct or actual concentration of oxygen in the exhaust gas is determined based on the value of the signal AFO1, as found in step 303. The routine proceeds to step 305 wherein a difference between the value of the signal AFO2, as sampled in step 301, and the value of the signal AFO2 on the reference output characteristic which corresponds to the concentration of oxygen, as determined in step 303, is calculated as the gain error β2 of the signal AFO2, as produced by the operational amplifier 39. The routine proceeds to step 306 wherein the value of the signal AFO2, as sampled in step 301, and the gain error β2, as determined in step 305, are stored in the memory of the microcomputer 20. The routine then terminates.

After the offset error β1 is derived in the virtual stoichiometric AFR measuring mode, and the gain error β2 is derived by calculation of an actual concentration of oxygen in the exhaust gas using the A/F output voltage AFO1, as produced by the operational amplifier 38, the microcomputer 20 interpolates values derived by adding the errors β1 and β2 to the reference output characteristic of the operational amplifier 39 to find the actual output characteristic of the operational amplifier 39. The interpolation may be achieved by a known manner using Eq. (1), and explanation thereof in detail will be omitted here. The microcomputer 20 compares the actual output characteristic with the reference output characteristic of the operational amplifier 39 to determine the output characteristic error of the operational amplifier 39. This enables an error of the stoichiometric AFR measuring signal AFO2 when the sensor element 10 is measuring the concentration of oxygen in the exhaust gas to be determined.

When it is required to determine an air-fuel ratio of the mixture to the engine, the microcomputer 20 enters an AFR measuring mode and samples an instantaneous value of the stoichiometric AFR measuring signal AFO2 outputted from the operational amplifier 39. The microcomputer 20 determines an error of the sampled value of the signal AFO2 (i.e., the sum of the offset and gain errors α1 and α2) based on the output characteristic error of the operational amplifier 39 and corrects the sampled value of the signal AFO2 so as to compensate for the error thereof and determines the concentration of oxygen (i.e., the A/F ratio) using the corrected value of the signal AFO2 in the narrow AFR measurement range (e.g., A/F=12 to 22).

The microcomputer 20 also works to calculate the actual output characteristic of the operational amplifier 38 using the interpolation techniques based on the reference output characteristic of the operational amplifier 38, the offset error α1, and the gain error α2, as derived in FIGS. 6 and 7, to determine an error of the AFR wide range measuring signal AFO1, as outputted from the operational amplifier 38 when the sensor element 10 is measuring the concentration of oxygen in the exhaust gas. Upon entering in the AFR measuring mode, the microcomputer 20 samples an instantaneous value of the signal AFO1 outputted from the operational amplifier 38, corrects it so as to compensate for the error between the sampled value and the reference output characteristic, and determines the concentration of oxygen (i.e., the A/F ratio) using the corrected value of the signal AFO1 in the full AFR measurement range (e.g., A/F=11 to air-to-fuel free ratio (i.e., an extremely lean A/F ratio)).

The microcomputer 20 of this embodiment is designed to find errors of outputs from the operational amplifiers 38 and 39, correct instantaneous outputs thereof to eliminate the errors, and determine A/F ratios of a mixture to the engine within the narrow AFR measurement range and the full AFR measurement range, thereby enhancing the accuracy of the air-fuel ratio feedback control and improving exhaust emissions of the engine.

Figure 9:
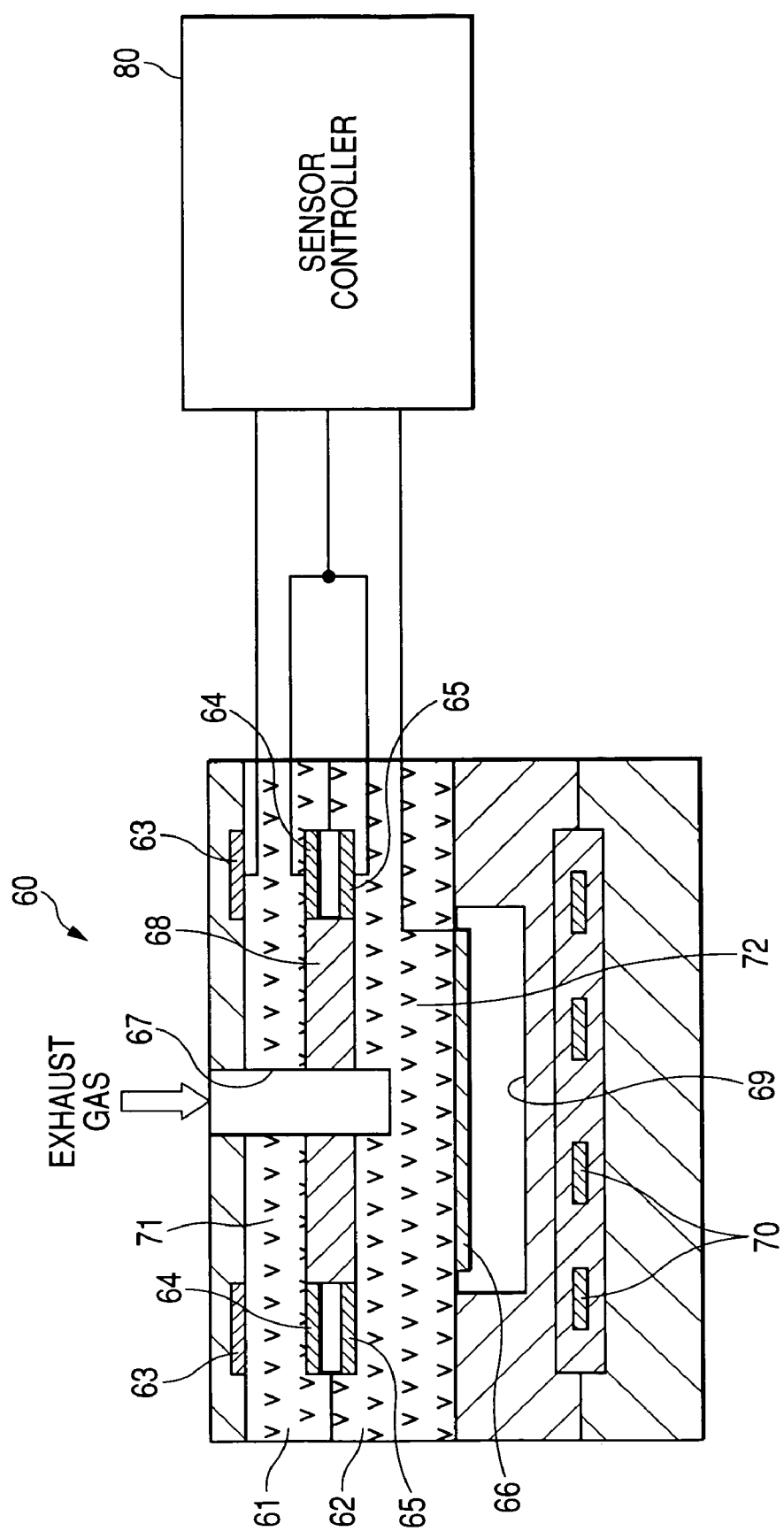
FIG. 9 is a transverse sectional view which shows a sensor element of a gas concentration measuring apparatus according to the second embodiment of the invention.

FIG. 9 shows a sensor element 60 according to the second embodiment of the invention which is different in structure from the one illustrated in FIG. 2 and may be fabricated in the A/F sensor as used in the first embodiment instead of the sensor element 10.

The sensor element 60 includes a laminate of two solid electrolyte layers 61 and 62. The solid electrolyte layer 61 has electrodes 63 and 64 affixed to opposed surfaces thereof. Similarly, the solid electrolyte layer 62 has electrodes 65 and 66 affixed to opposed surfaces thereof. Each of the electrodes 63, 64, and 65 is viewed in the drawing as being made up of right and left separate parts, but, it is, in practice, formed by a single plate having a connecting portion (not shown) extending in a transverse direction in the drawing.

The solid electrolyte layer 61 and the electrodes 63 and 64 constitute a pump cell 71. The solid electrolyte layer 62 and the electrodes 65 and 66 constitute a monitor cell 72. The electrodes 63 to 66 are joined to a sensor control circuit 80 which leads to the microcomputer 20, as illustrated in FIG. 1.

The sensor element 60 also includes a gas inlet 67 through which exhaust gasses of the automotive engine enter and a porous diffusion layer 68, an air duct 69, and a heater 70. The structure and operation of this type of sensor element are disclosed in, for example, U.S. Pat. No. 6,295,862 B1, assigned to the same assignee as that of this application, disclosure of which is incorporated herein by reference. The monitor cell 72 is generally also called an electromotive force cell or an oxygen concentration sensor cell.

The monitor cell 72 works to produce an electromotive force which has one of two discrete values (e.g., 0V and 0.9V) selectively as a function of whether the exhaust gasses are on the rich side or the lean side of a stoichiometric point corresponding to a stoichiometric air-fuel ratio of mixture supplied to the engine. When the exhaust gasses are on the lean side, the monitor cell 72 produces a lower electromotive force. Conversely, when the exhaust gasses are on the rich side, the monitor cell 72 produces a higher electromotive force. The sensor control circuit 80 works to control the voltage applied to the pump cell 71 so that an electromotive force produced by the monitor cell 72 is kept at 0.45V which corresponds to the stoichiometric point.

Figure 10:
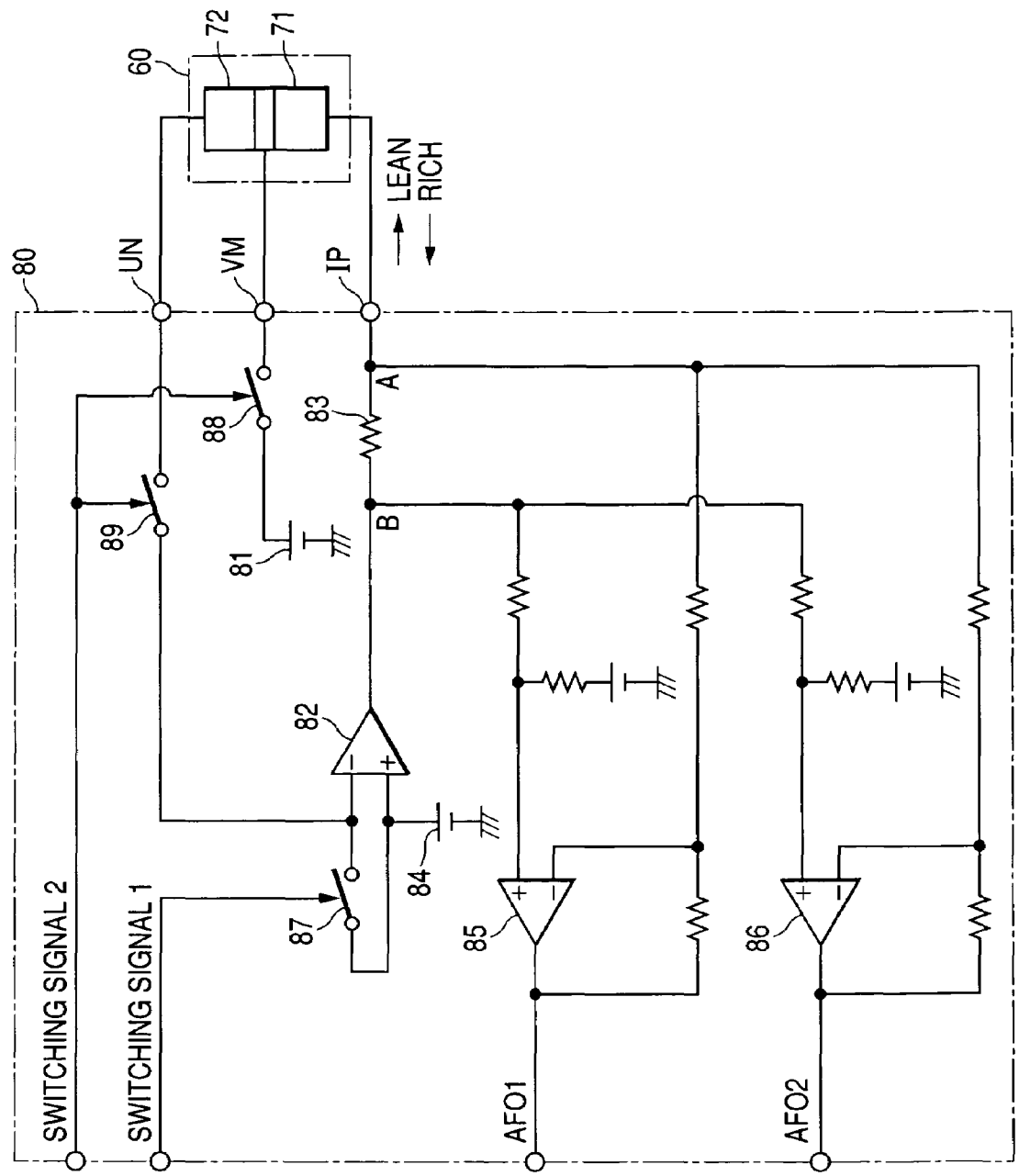
FIG. 10 is a circuit diagram which shows a sensor control circuit connected to the sensor element of FIG. 9.

FIG. 10 shows an internal structure of the sensor control circuit 80, as illustrated in FIG. 9.

A terminal VM is a common terminal shared between the pump cell 71 and the monitor cell 72. The common terminal VM is connected to a reference voltage source 81 which produces a reference voltage of, for example, 2.5V. The pump cell 71 is also connected at the electrode 63 to the terminal LP. The monitor cell 72 is also connected at the electrode 66 to the terminal UN. The terminals IP and UN form a closed circuit together with the cells 71 and 72, an operational amplifier 82, and a current-measuring resistor 83. The operational amplifier 82 is connected at a noninverting input (i.e., +terminal) thereof to a reference voltage source 84 which produces a reference voltage of 3.0V.

When the exhaust gas is lean, the current Ip flows through the current-measuring resistor 83 in the direction from the junction B to the junction A. Conversely, when the exhaust gas is rich, the current Ip flows through the current-measuring resistor 83 in the direction from the junction A to the junction B. The sensor control circuit 80 also includes a feedback circuit (not shown) which works to control the voltage applied to the pump cell 71 to bring an output voltage of the monitor cell 72 into agreement with a target one. This feedback control can be of any type known in the art, and explanation thereof in detail will be omitted here.

The sensor control circuit 80 also includes operational amplifiers 85 and 86, and switches 87, 88, and 89. The operational amplifier 85 is connected to the junctions A and B across the current-measuring resistor 83 and works to output the A/F output voltage AFO1 within the full AFR measurement range to the microcomputer 20, as illustrated in FIG. 1. Similarly, the operational amplifier 86 is connected to the junctions A and B across the current-measuring resistor 83 and works to output the A/F output voltage AFO2 within the narrow AFR measurement range to the microcomputer 20, as illustrated in FIG. 1. Like the first embodiment, the operational amplifier 85 is smaller in amplification factor than the operational amplifier 86.

The switch 87 is connected to plus and minus inputs of the operational amplifier 82. The switch 88 is connected to the common terminal VM. The switch 89 is connected to the monitor cell terminal UN. The switch 87 is of a normally open type and controlled in operation by a switching signal 1. Each of the switches 88 and 89 is of a normally closed type and controlled in operation by a switching signal 2.

In the AFR measuring mode, the sensor control circuit 80 works to open the switch 87, while closing the switches 88 and 89 to produce the A/F output voltages AFO1 and AFO2 as a function of an instantaneous air-fuel ratio of a mixture supplied to the engine. In the virtual stoichiometric AFR measuring mode, the sensor control circuit 80 works to close the switch 87, while opening the switches 88 and 89 and sample instantaneous values of the A/F output voltage AFO1 and AFO2 to determine the offset errors α1 and β1 in the same manner as described in the first embodiment. The sensor control circuit 80 also calculates the gain errors α2 and β2 in the same manner as described in the first embodiment. Other arrangements are identical with those in the first embodiment, and explanation thereof in detail will be omitted here.

Figure 11:
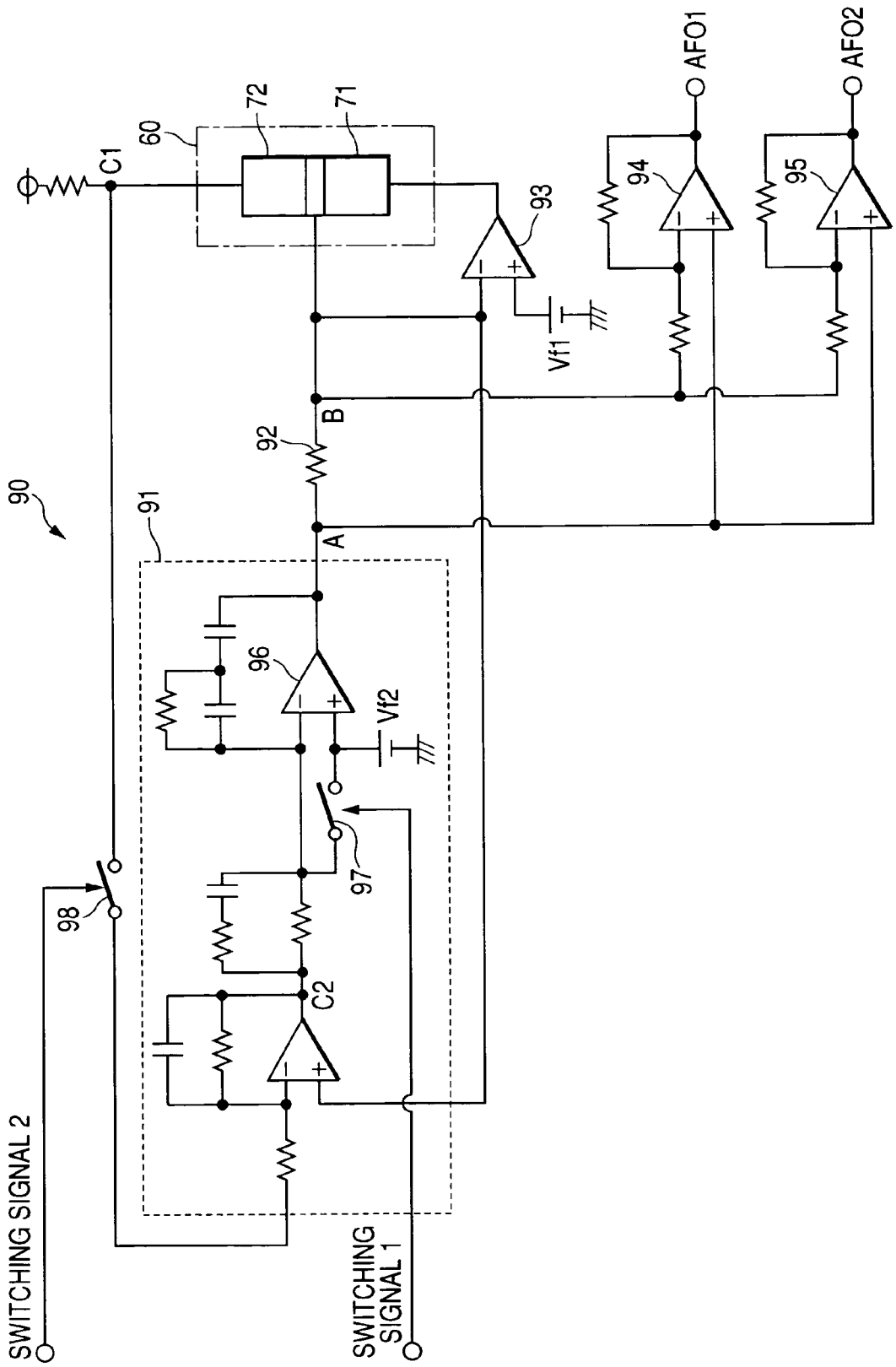
FIG. 11 is a circuit diagram which shows a modification of the sensor control circuit of FIG. 10.

In the sensor control circuit 80, the voltages developed at the junctions A and B located across the current-measuring resistor 83 both change with a change in current flowing through the current-measuring resistor 83. One of ends of the current-measuring resistor 83 may, however, be maintained constant using the structure, as illustrated in FIG. 11.

The sensor control circuit 90 includes an operational amplifier 93 through which the same voltage (e.g., 3V) as the reference voltage Vf1 is applied to a common terminal of the pump cell 71 and the monitor cell 72 of the sensor element 60. This causes the voltage appearing at the junction B to be kept at 3V, for example. The sensor control circuit 90 has a closed loop including the monitor cell 72, the feedback circuit 91, and the current-measuring resistor 92. The reference voltage Vf2 provided in the feedback circuit 91 is, for example, 2.55V.

The operation of the sensor control circuit 90 will be described taking as an example a case in which the exhaust gas of the engine is rich.

When the exhaust gas is rich, the monitor cell 72 produces an electromotive force, so that the voltage appearing at a junction C1 rises up to, for example, 3.45V, thereby causing the electric potential developed at a junction C2 in the feedback circuit 91 to drop. This causes the electric potential at the junction A to rise. Specifically, when the exhaust is rich, the sensor element current Ip flows through the current-measuring resistor 92 from the junction A to the junction B. Conversely, when the exhaust is lean, the sensor element current Ip flows through the current-measuring resistor 92 from the junction B to the junction A.

The sensor control circuit 90 also includes operational amplifiers 94 and 95 which are different in amplification factor from each other. The operational amplifier 94 is connected to the junctions A and B of the current-measuring resistor 92 and works to output the A/F output voltage AFO1 within the full AFR measurement range to the microcomputer 20, as illustrated in FIG. 1. Similarly, the operational amplifier 95 is connected to the junctions A and B of the current-measuring resistor 92 and works to output the A/F output voltage AFO2 within the narrow AFR measurement range to the microcomputer 20, as illustrated in FIG. 1. The The feedback circuit 91 includes the operational amplifier 96 and the switch 97. The switch 97 is connected to plus and minus inputs of the operational amplifier 96. The switch 98 is disposed between the feedback circuit 91 and the monitor cell 72. The switch 97 is of a normally open type and controlled in operation by the switching signal 1. The switch 98 is of a normally closed type and controlled in operation by the switching signal 2.

In the AFR measuring mode, the sensor control circuit 90 works to open the switch 97, while closing the switch 98 to produce the A/F output voltages AFO1 and AFO2 as a function of an instantaneous air-fuel ratio of a mixture supplied to the engine. In the virtual stoichiometric AFR measuring mode, the sensor control circuit 90 works to close the switch 97, while opening the switch 98 and sample instantaneous values of the A/F output voltage AFO1 and AFO2 to determine the offset errors α1 and β1 in the same manner as described in the first embodiment. The sensor control circuit 90 also calculates the gain errors α2 and β2 in the same manner as described in the first embodiment. Other arrangements are identical with those in the first embodiment, and explanation thereof in detail will be omitted here.

Figure 12:
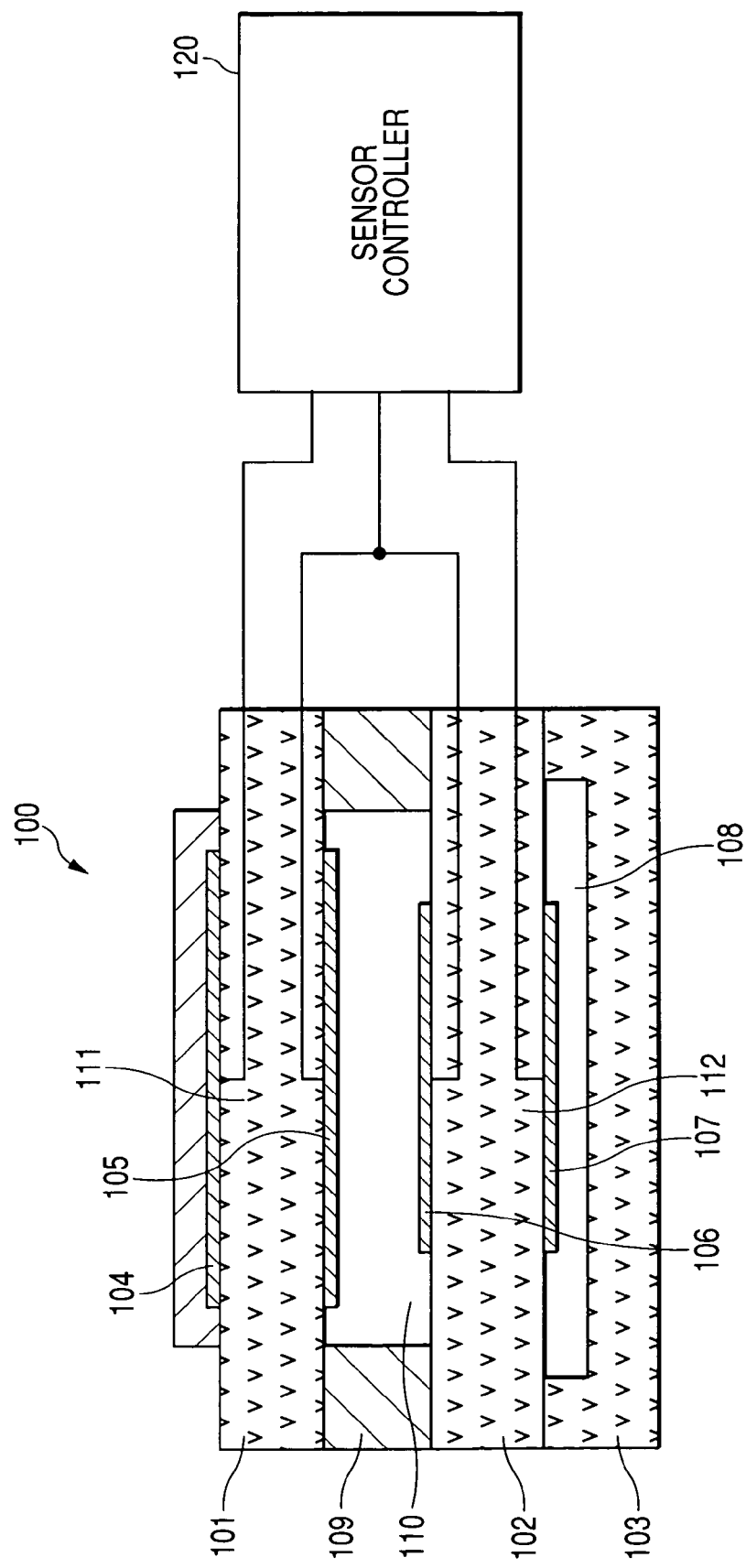
FIG. 12 is a transverse sectional view which shows a modified form of a sensor element which may be employed in a gas concentration measuring apparatus of each embodiment.

FIG. 12 shows a sensor element 100 which may be built in the A/F sensor, as employed in each of the above embodiments.

The sensor element 100 includes three solid electrolyte layers 101, 102, and 103. The solid electrolyte layer 101 has electrodes 104 and 105 affixed to opposed surfaces thereof. Similarly, the solid electrolyte layer 102 has electrodes 106 and 107 affixed to opposed surfaces thereof. The solid electrolyte layer 101 and the electrodes 104 and 105 form a pump cell 111. The solid electrolyte layer 102 and the electrodes 106 and 107 form a monitor cell 112. The solid electrolyte layer 103 forms a wall defining an oxygen reference chamber 108. The sensor element 100 is, like the sensor element 10, of a laminated structure. The sensor element 100 also includes a porous diffusion layer 109 and a gas chamber 110 into which exhaust gasses of the automotive engine enter. The monitor cell 112 operates, like the monitor cell 72 illustrated in FIG. 9, as an electromotive force cell or an oxygen concentration sensor cell.

The sensor element 10 is connected to the sensor control circuit 120. The sensor control circuit 120 may have substantially the same structure as the one illustrated in FIG. 10 or 11, and explanation thereof in detail will be omitted here.

The A/F sensor, as employed in each of the above embodiments, may also be designed to have two- or three-cell structure. The sensor element 10, 60, or 100 may be of a cup-shaped type known in the art. The A/F sensor may also be implemented by a typical $O_2$ sensor designed to produce an electromotive force between electrodes affixed to a sensor element as a function of concentration of oxygen contained in exhaust emissions of an automotive engine.

The gas concentration measuring apparatus, as described in each of the above embodiments, may be used with a composite gas concentration measuring sensor which includes first and second cells made of a solid electrolyte body. The first cell works as a pump cell to pump oxygen molecules out of or into a first gas chamber formed in a sensor body and output a signal indicative of the concentration of the pumped oxygen molecules. The second cell works as a sensor cell to produce a signal indicative of the concentration of a preselected component of gasses flowing into a second gas chamber from the first gas chamber. For example, the composite gas concentration measuring sensor may be used to measure the concentration NOx contained in exhaust gasses of the automotive engine. Further, the composite gas concentration measuring sensor may be designed to have a third cell serving as a monitor cell or a second pump cell to produce an electromotive force as a function of concentration of oxygen molecules remaining in the second gas chamber.

The virtual stoichiometric AFR measuring mode may alternatively be achieved in the sensor control circuits 30, 80, 90, or 120 in the following manner.

For instance, the switch 35 of the sensor control circuit 30 of FIG. 1 connected to the output of the operational amplifier 34 leading to the sensor element 10 is opened to block the flow of the sensor element current Ip to the sensor control circuit 30. This causes a reference sensor element current of 0 mA indicating a 0% concentration of oxygen in the exhaust gas to be created. The sensor control circuit to receive the A/F output voltages AFO1 and AFO2 as a function of an output of 0 mA from the sensor element 10. In other words, the sensor control circuit 30 works to open-circuits the sensor element 10 to place itself in a condition equivalent to when measuring a 0% concentration of oxygen in the exhaust gas. The switching between the on-state and off-state of the switch 35 may be accomplished using a switching element such as a transistor.

The virtual stoichiometric AFR measuring mode may alternatively be accomplished by connecting a current measuring resistor, such as the one 32 of FIG. 1, to one of the plus and minus terminals of the sensor element 10, installing a switch to the other terminal, and opening the switch to open-circuit an electrical circuit extending across the sensor element 10.

The virtual stoichiometric AFR measuring mode may also be accomplished by place joining terminals of, for example, the sensor control circuit 30 leading to the plus and minus terminals of the sensor element 10 at the same electrical potential, so that 0V may be applied to the sensor element 10. This causes 0 mA to flow through the sensor element 10.

The microcomputer 20 may alternatively be designed to calculate two actual concentrations of oxygen within the narrow AFR measuring range of 12 to 22 in terms of the air-fuel ratio using the AFR wide range measuring signal AFO1, find two errors of the stoichiometric AFR measuring signal AFO2 at the actual concentrations of oxygen to determine an error between the actual output characteristic and the reference output characteristic of the operational amplifier 39 through the interpolation, as described above, and correct a sampled instantaneous value of the stoichiometeric AFR measuring signal AFO2 so as to compensate for such an error. This is suitable for the case where it is difficult to place the sensor control circuit 30 in the virtual stoichiometric AFR measuring mode.

The gas concentration measuring apparatus may alternatively be designed to measure the concentration of HC or CO contained in the exhaust gasses of the automotive engine. The measurement of concentration of HC or CO is achieved by pumping excessive oxygen ($O_2$) out of the first gas chamber using the pump cell and decomposing HC or CO contained in the gasses entering the second gas chamber using the sensor cell to produce an electric signal indicative of the concentration of HC or CO.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas concentration measuring apparatus designed to sample an output of a gas concentration sensor which includes a sensor element made of a solid electrolyte body working to produce an electric current as a function of concentration of a given gas component, comprising:

a first signal output circuit designed to output a first sensor signal as a function of an electric current produced by the sensor element for use in determining a concentration of the given gas component in a first gas concentration range;

a second signal output circuit designed to output a second sensor signal as a function of the electric current for use in determining a concentration of the given gas component in a second gas concentration range different from the first gas concentration range; and a gas concentration determining circuit configured to sample the first and second sensor signals to determine the concentrations of the given gas component in the first and second gas concentration ranges, said gas concentration determining circuit analyzing a value of the first sensor signal to determine a first output characteristic error that is a difference between an actual output characteristic and a stated reference output characteristic of said first signal output circuit, sampling values of the first sensor signal and the second sensor signals when the gas component lies within the second gas concentration range, calculating an actual concentration of the gas component using a concentration of the gas component indicated by the sampled value of the first sensor signal and the first output characteristic error, determining a difference between the value of he second sensor signal sampled upon calculation of the actual concentration of the gas component and a corresponding value of a stated reference output characteristic of the second signal output circuit as a second output characteristic error of the second signal output circuit.

2. A gas concentration measuring apparatus as set forth in claim 1, wherein said gas concentration determining circuit samples values of the first sensor signal at two different concentrations of the gas component and determines two output errors that are differences between the sampled values of the first sensor signal and corresponding values of the stated reference output characteristic of said first signal output circuit, said gas concentration determining circuit calculating the actual concentration of the gas component within the second gas concentration range using the determined two output errors.

3. A gas concentration measuring apparatus as set forth in claim 2, wherein said gas concentration determining circuit performs an interpolation operation on the two output errors of the first sensor signal to determine the actual concentration of the given gas component within the second gas concentration range.

4. A gas concentration measuring apparatus as set forth in claim 2, wherein the gas component is oxygen, the first gas concentration range being between a 0% oxygen concentration and an air equivalent concentration that is a concentration of the oxygen equivalent to that of atmospheric air, and wherein said gas concentration determining circuit samples values of the first sensor signal at the 0% oxygen concentration and the air equivalent concentration to determine the two output errors.

5. A gas concentration measuring apparatus as set forth in claim 4, further comprising a sensor control circuit and a switching circuit, said sensor control circuit including said first and second signal output circuits and working to apply a voltage to the sensor element to produce a flow of the electric current through the sensor element, said sensor control circuit operating in a first mode to sample the first and second sensor signals for use in determining the concentrations of the oxygen in the first and second gas concentration ranges and in a second mode to produce a reference sensor signal that is the value of the first sensor signal and indicates the 0% oxygen concentration, said switch working to switch between the first and second modes of said sensor control circuit when requested.

6. A gas concentration measuring apparatus as set forth in claim 4, wherein said gas concentration determining circuit samples a value of the second sensor signal at the 0% oxygen concentration and determines an output error that is a difference between the sampled value of the second sensor signal and a corresponding value of the stated reference output characteristic of said second signal output circuit and an output error that is a difference between the value of the second sensor signal sampled upon calculation of the actual concentration of the oxygen and a corresponding value of the stated reference output characteristic of said second signal output circuit, further comprising a correction circuit working to correcting a sampled value of the second signal output so as to compensate for the output errors of the second sensor signal.

7. A gas concentration measuring apparatus as set forth in claim 1, wherein said gas concentration determining circuit is designed to sample values of the first sensor signal at two concentrations of the gas component within the second gas concentration range to determine two actual concentrations of the gas component using the first output characteristic error, said gas concentration determining circuit determining two output errors that are differences between the sampled values of the first sensor signal and corresponding values of the stated reference output characteristic of the first signal output circuit and calculating the second output characteristic error using the two output errors, further comprising a correction circuit working to correct a sampled value of the second signal output so as to compensate for the second output characteristic error.

8. A gas concentration measuring apparatus as set forth in claim 1, wherein said first signal output circuit is designed to amplify an input thereto that is a function of the electrical current produced by the sensor element at a first amplification factor to output the first sensor signal, the second signal output being designed to amplify an input thereto that is a function of the electrical current produced by the sensor element at a second amplification factor different from the first amplification factor to output the second sensor signal.

9. A gas concentration measuring apparatus as set forth in claim 8, wherein the first amplification factor is smaller than the second amplification factor.

10. A gas concentration measuring apparatus designed to sample an output of a gas concentration sensor which includes a sensor element made of a solid electrolyte body working to produce an electric current as a function of concentration of oxygen of exhaust emissions of an internal combustion engine, comprising:

a first signal output circuit designed to output a first sensor signal as a function of the electric current for use in determining a concentration of the oxygen in a wide concentration range including a stoichiometric oxygen concentration equivalent to a 0% oxygen concentration and an air equivalent concentration that is a concentration of oxygen equivalent to that of atmospheric air;

a second signed output circuit designed to output a second sensor signal as a function of the electric current for use in determining a concentration of the oxygen in a narrow concentration range including the stoichiometric oxygen concentration and excluding the air equivalent concentration; and a gas concentration determining circuit configured to sample the first and second sensor signals to determine the concentrations of the oxygen in the first and second gas concentration ranges, said gas concentration determining circuit sampling values of the first sensor signal at the stoichiometric oxygen concentration and the air equivalent concentration, determining two output errors that are differences between the sampled values of the first sensor signal and corresponding values of a stated reference output characteristic of said first signal output circuit as a first output characteristic error of said first signal output circuit, sample values of the first sensor signal and the second sensor signals when the concentration of the oxygen lies within the second gas concentration range, calculating an actual concentration of the oxygen using a concentration of the oxygen indicated by the sampled value of the first sensor signal and the first output characteristic error of said first signal output circuit, and determining a difference between the value of the second sensor signal sampled upon calculation of the actual concentration of the oxygen and a corresponding value of a stated reference output characteristic of the second signal output circuit as a second output characteristic error of the second signal output circuit.

11. A gas concentration measuring apparatus as set forth in claim 10, further comprising a sensor control circuit and a switching circuit, said sensor control circuit including said first and second signal output circuits and working to apply a voltage to the sensor element to produce a flow of the electric current through the sensor element, said sensor control circuit operating in a first mode to sample the first and second sensor signals for use in determining the concentrations of the oxygen in the first and second gas concentration ranges and in a second mode to produce a reference sensor signal that is the value of the first sensor signal and indicates the 0% oxygen concentration, said switch working to switch between the first and second modes of said sensor control circuit when requested.

12. A gas concentration measuring apparatus as set forth in claim 11, wherein said gas concentration determining circuit samples a value of the second sensor signal at the 0% oxygen concentration and determines an output error that is a difference between the sampled value of the second sensor signal and a corresponding value of the stated reference output characteristic of said second signal output circuit and an output error that is a difference between the value of the second sensor signal sampled upon calculation of the actual concentration of the oxygen and a corresponding value of the stated reference output characteristic of said second signal output circuit, further comprising a correction circuit working to correcting a sampled value of the second signal output so as to compensate for the output errors of the second sensor signal.

13. A gas concentration measuring apparatus as set forth in claim 10, wherein said gas concentration determining circuit is designed to sample values of the first sensor signal at two concentrations of the oxygen within the second gas concentration range to determine two actual concentrations of the oxygen using the first output characteristic error, said gas concentration determining circuit determining two output errors that are differences between the sampled values of the first sensor signal and corresponding values of the stated reference output characteristic of the first signal output circuit and calculating the second output characteristic error using the two output errors, further comprising a correction circuit working to correct a sampled value of the second signal output so as to compensate for the second output characteristic error.

14. A gas concentration measuring apparatus as set forth in claim 10, wherein said first signal output circuit is designed to amplify an input thereto that is a function of the electrical current produced by the sensor element at a first amplification factor to output the first sensor signal, the second signal output being designed to amplify an input thereto that is a function of the electrical current produced by the sensor element at a second amplification factor different from the first amplification factor to output the second sensor signal.

15. A gas concentration measuring apparatus as set forth in claim 14, wherein the first amplification factor is smaller than the second amplification factor.

16. A gas concentration measuring apparatus designed to sample an output of a gas concentration sensor which includes a sensor element made of a solid electrolyte body working to produce an electric current as a function of concentration of a given gas component, comprising:
  a first signal output circuit designed to output a first sensor signal as a function of an electric current produced by the sensor element for use in a determining a concentration of the given gas component in a first gas concentration range;
  a second signal output circuit designed to output a second sensor signal as a function of the electric current for use in determining a concentration of the given gas component in a second gas concentration range different from the first gas concentration range; and
  a gas concentration determining circuit configured to sample the first and second sensor signals to determine the concentrations of the given gas component in the first and second gas concentration ranges, said gas concentration determining circuit analyzing a value of the first sensor signal to determine a first characteristic error that is a difference between an actual output characteristic and a stated reference output characteristic of said first signal output circuit, sampling values of the first sensor signal and the second sensor signals when the gas component lies within the second gas concentration range, calculating an actual concentration of the gas component using a concentration of the gas component indicated by the sampled value of the first sensor signal and the first output characteristic error, determining a difference between the value of the second sensor signal and a corresponding value of a stated reference output characteristic of the second signal output circuit as a second output characteristic error of the second signal output circuit, the corresponding value of the stated reference output characteristic of the second signal output circuit being determined based on the actual concentration of the gas component using the concentration of the gas component indicated by the sampled value of the first sensor signal and the first output characteristic error.

17. A gas concentration measuring apparatus as set forth in claim 16, wherein said gas concentration determining circuit samples values of the first sensor signal at two different concentrations of the gas component and determines two output errors that are differences between the sampled values of the first sensor signal and corresponding values of the stated reference output characteristic of said first signal output circuit, said gas concentration determining circuit calculating the actual concentration of the gas component within the second gas concentration range using the determined two output errors.

18. A gas concentration measuring apparatus as set forth in claim 17, wherein said gas concentration determining circuit performs an interpolation operation on the two output errors of the first sensor signal to determine the actual concentration of the given gas component within the second gas concentration range.

19. A gas concentration measuring apparatus as set forth in claim 17, wherein the gas component is oxygen, the first gas concentration range being between a 0% oxygen concentration and an air equivalent concentration that is a concentration of the oxygen equivalent to that of atmospheric air, and wherein said gas concentration determining circuit samples values of the first sensor signal at the 0% oxygen concentration and the air equivalent concentration to determine the two output errors.

20. A gas concentration measuring apparatus as set forth in claim 16, wherein said gas concentration determining circuit is designed to sample values of the first sensor signal at two concentrations of the gas component within the second gas concentration range to determine two actual concentrations of the gas component using the first output characteristic error, said gas concentration determining circuit determining two output errors that are differences between the sampled values of the first sensor signal and corresponding values of the stated reference output characteristic of the first signal output circuit and calculating the second output characteristic error using the two output errors, further comprising a correction circuit working to correct a sampled value of the second signal output so as to compensate for the second output characteristic error.

21. A gas concentration measuring apparatus designed to sample an output of a gas concentration sensor which includes a sensor element made of a solid electrolyte body working to produce an electric current as a function of concentration of oxygen of exhaust emissions of an internal combustion engine, comprising:

a first signal output circuit designed to output a first sensor signal as a function of the electric current for use in determining a concentration of the oxygen in a wide concentration range including a stoichiometric oxygen concentration equivalent to a 0% oxygen concentration and an air equivalent concentration that is a concentration of oxygen equivalent to that of atmospheric air;

a second signal output circuit designed to output a second sensor signal as a function of the electric current for use in determining a concentration of the oxygen in a narrow concentration range including the stoichiometric oxygen concentration and excluding the air equivalent concentration; and a gas concentration determining circuit configured to sample the first and second sensor signals to determine the concentrations of the oxygen in the first and second gas concentration ranges, said gas concentration determining circuit sampling values of the first sensor signal at the stoichiometric oxygen concentration and the air equivalent concentration, determining two output errors that are differences between the sampled values of the first sensor signal and corresponding values of a stated reference output characteristic of said first signal output circuit as a first output characteristic error of said first signal output circuit, sampling values of the first sensor signal and the second sensor signals when the concentration of the oxygen lies within the second gas concentration range, calculating an actual concentration of the oxygen using a concentration of the oxygen indicated by the sampled value of the first sensor signal and the first output characteristic error of said first signal output circuit, and determining a difference between the value of the second sensor and a corresponding value of a stated reference output characteristic of the second signal output circuit as a second output characteristic error of the second signal output circuit, the corresponding value of the stated reference output characteristic of the second signal output circuit being determined based on the actual concentration of oxygen using the concentration of the oxygen indicated by the sampled value of the first sensor signal and the first output characteristic error.

22. A gas concentration measuring apparatus as set forth in claim 21, wherein said gas concentration determining circuit is designed to sample values of the first sensor signal at two concentrations of the oxygen within the second gas concentration range to determine two actual concentrations of the oxygen using the first output characteristic error, said gas concentration determining circuit determining two output errors that are differences between the sampled values of the first sensor signal and corresponding values of the stated reference output characteristic of the first signal output circuit and calculating the second output characteristic error using the two output errors, further comprising a correction circuit working to correct a sampled value of the second signal output so as to compensate for the second output characteristic error.

* * * * *